(12) United States Patent
Xavier Da Silveira et al.

(10) Patent No.: US 10,863,935 B2
(45) Date of Patent: Dec. 15, 2020

(54) APPARATUS AND METHOD FOR OPTICAL TISSUE DETECTION

(71) Applicant: BSX ATHLETICS, Austin, TX (US)

(72) Inventors: Paulo E. Xavier Da Silveira, Boulder, CO (US); Nithin O. Rajan, Austin, TX (US); Dustin M. Freckleton, Austin, TX (US)

(73) Assignee: Happy Health, Inc., Los Angeles, CA (US)

( * ) Notice: Subject to any disclaimer, the term of this patent is extended or adjusted under 35 U.S.C. 154(b) by 354 days.

(21) Appl. No.: 15/261,591

(22) Filed: Sep. 9, 2016

(65) Prior Publication Data

US 2017/0071518 A1 Mar. 16, 2017

Related U.S. Application Data

(60) Provisional application No. 62/217,679, filed on Sep. 11, 2015.

(51) Int. Cl.
| | | |
|---|---|---|
| *A61B 5/00* | (2006.01) | |
| *A61B 5/1455* | (2006.01) | |
| *A61B 5/145* | (2006.01) | |
| *A61B 5/11* | (2006.01) | |

(52) U.S. Cl.
CPC ........ *A61B 5/14552* (2013.01); *A61B 5/0022* (2013.01); *A61B 5/1118* (2013.01); *A61B 5/14542* (2013.01); *A61B 5/14546* (2013.01); *A61B 5/681* (2013.01); *A61B 5/6844* (2013.01); *A61B 5/7405* (2013.01); *A61B 5/746* (2013.01); *A61B 5/7455* (2013.01)

(58) Field of Classification Search
CPC ... A61B 5/14552; A61B 5/6844; A61B 5/681; A61B 5/1118; A61B 5/7455; A61B 5/0022; A61B 5/746; A61B 5/14546; A61B 5/7405; A61B 5/14542
See application file for complete search history.

(56) References Cited

U.S. PATENT DOCUMENTS

| | | | | |
|---|---|---|---|---|
| 2010/0278441 | A1* | 11/2010 | Shashidhar | G01J 3/32 382/218 |
| 2013/0096403 | A1* | 4/2013 | Dacso | A61B 5/14551 600/324 |
| 2014/0006830 | A1* | 1/2014 | Kamhi | G06F 1/3287 713/324 |
| 2014/0155753 | A1* | 6/2014 | McGuire, Jr. | A61B 5/6833 600/473 |
| 2015/0148623 | A1* | 5/2015 | Benaron | A61B 5/0059 600/306 |
| 2016/0072802 | A1* | 3/2016 | Hoyos | H04L 63/0861 726/5 |
| 2016/0321846 | A1* | 11/2016 | Pham | G07C 9/00007 |

* cited by examiner

*Primary Examiner* — Navin Natnithithadha
*Assistant Examiner* — Andrey Shostak
(74) *Attorney, Agent, or Firm* — Polsinelli PC

(57) ABSTRACT

Apparatus for optical tissue detection and discrimination between a tissue of a user and non-tissue materials and method of optical tissue detection and discrimination between a tissue of a user and non-tissue materials are provided. The apparatus for optical tissue detection includes one or more of light sources. The apparatus can further include at least one photodetector. A processor can be operable to determine whether the detected light is from a tissue of a user.

12 Claims, 26 Drawing Sheets

APPARATUS AND METHOD FOR OPTICAL TISSUE DETECTION

CROSS-REFERENCE TO RELATED APPLICATIONS

This application claims benefit of provisional application 62/217,679 filed Sep. 11, 2015, said application is expressly incorporated by reference herein in its entirety.

FIELD

The present disclosure relates to an optical tissue detection apparatus and method for detecting a tissue using the optical tissue detection apparatus.

BACKGROUND

Monitoring exertion via a heart rate monitor has long been a centerpiece of training for professional and performance athletes, as well as amateurs and retired players. Additional tests can be performed on the individual and involve taking measurements of the individual by a professional. For example, some methods involve drawing of blood from the individual. Specifically, in order to measure lactate, the individual has blood drawn and tests performed to determine the lactate in the blood at the specified time.

BRIEF DESCRIPTION OF THE DRAWINGS

Implementations of the present technology will now be described, by way of example only, with reference to the attached figures. It is to be noted, however, that the appended drawings are not to be considered limiting scope of the present disclosure.

DETAILED DESCRIPTION

Figure 1:
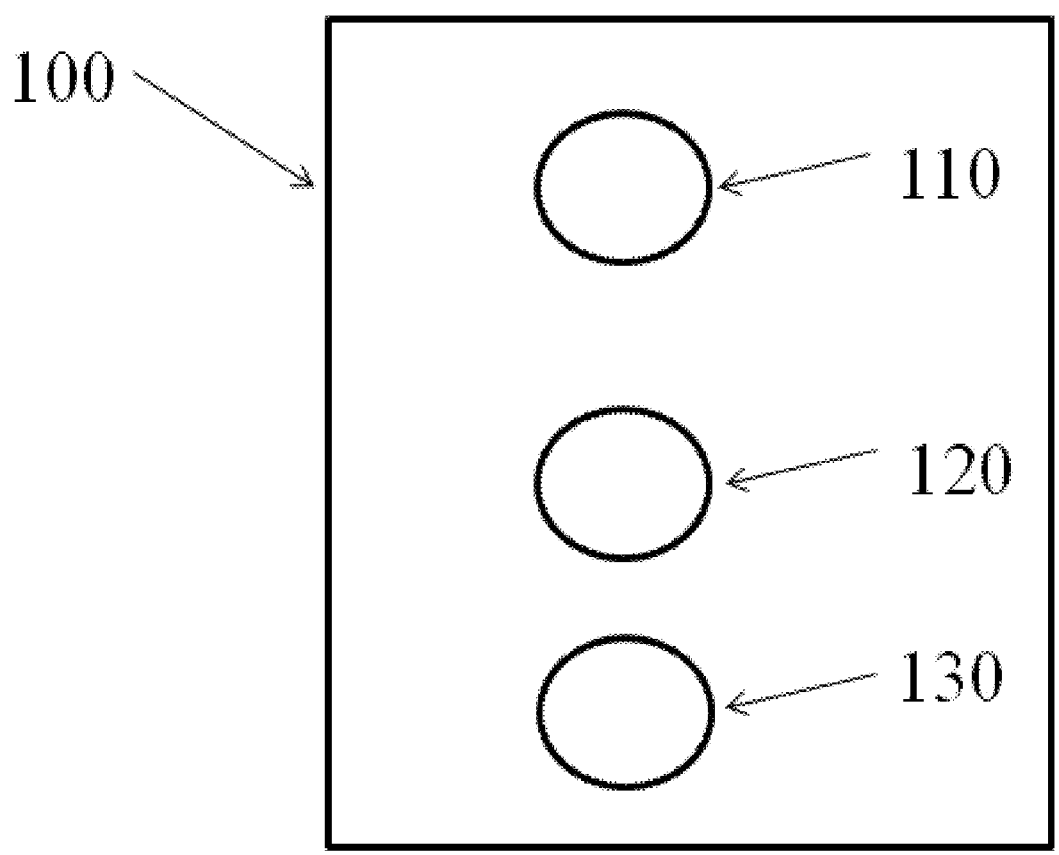
FIG. 1 is a schematic diagram optical-electronic sensor array operable to detect tissue according to the present disclosure.

Various examples of the disclosure are discussed in detail below. While specific implementations are discussed, it should be understood that this is done for illustration purposes only. A person skilled in the relevant art will recognize that other components and configurations can be used without parting from the spirit and scope of the disclosure.

It should be understood at the outset that although illustrative implementations of one or more examples are illustrated below, the disclosed apparatus and method can be implemented using any number of techniques. The disclosure should in no way be limited to the illustrative implementations, drawings, and techniques illustrated herein, but can be modified within the scope of the appended claims along with their full scope of equivalents.

Unless otherwise specified, any use of any form of the terms "connect," "engage," "couple," "attach," or any other term describing an interaction between elements is not meant to limit the interaction to direct interaction between the elements and also can include indirect interaction between the elements described. In the following discussion and in the claims, the terms "including" and "comprising" are used in an open-ended fashion, and thus should be interpreted to mean "including, but not limited to . . . ". The various characteristics described in more detail below, will be readily apparent to those skilled in the art with the aid of this disclosure upon reading the following detailed description, and by referring to the accompanying drawings. The term "substantially" is defined to be essentially conforming to the particular dimension, shape or other word that substantially modifies, such that the component need not be exact. For example, substantially cylindrical means that the object resembles a cylinder, but can have one or more deviations from a true cylinder. The term "about" when used to refer to a range includes values that can be slightly above or below the range. For example, "about" can refer to the extension of the range based on the order of significant digits that are used. The use of the term about does not require the range to extend beyond the values indicated, whereby there is explicit support for the range listed in exact values. The term "close" refers to the proximity of an object to another object. This can be such that the objects almost or do touch at least partially. In other examples, an object is close to another object when there is no object between the two objects. In general, the term close refers to a short distance, which is relative to the size of the objects involved.

The present disclosure generally relates to a non-invasive optical-electronic device operable to determine the presence of a tissue. A tissue as used herein refers to a group of biological cells that perform a similar function. In at least one example, the non-invasive optical-electronic device can also be operable to determine a level of a biological indicator within tissue or blood vessels. Examples of non-invasive optical-electronic devices operable to determine biological indicators are described in U.S. Pat. No. 8,996,088 entitled APPARATUS AND METHOD FOR IMPROVING TRAINING THRESHOLD, the entire contents of which are incorporated herein by reference. The optical-electronic device can be used by itself or in combination with other optical-electronic devices or biosensors. The present non-invasive sensing devices can optionally be operable to detect physiological parameters, such as muscle tissue oxygenation parameters, concentration of oxygenated hemoglobin, deoxygenated hemoglobin, and total hemoglobin concentration, degree of hydration, and lactate concentration. The present non-invasive sensing device can be implemented using Near InfraRed Spectroscopy (NIRS) as a radiation source. The present non-invasive sensing device can further include a detector configured for receiving NIRS signals and subsequent detection thereof. The present disclosure allows for tissue detection across a wide range of skin contact area. For example, the present disclosure allows for tissue detection on a calf, head, thigh, arm, and the like.

FIG. 1 illustrates a non-invasive optical-electronic device 100, according to an example of the present disclosure. The device 100 can be placed in direct contact with a portion of a user, such as a calf, wrist, forearm, or head. The device 100 can be placed and secured in direct contact with a portion of a user, such as a calf, wrist, forearm, or head. In at least one example, a strap, a sleeve, a wrap, a portion of an article of clothing such as a pant leg, a shirt sleeve, a jacket, a sock, a visor or hat, or any other suitable article of clothing can affix the device 100 to the user. In other implementations, the device 100 can be operable to receive touch or be held temporarily in contact with a user or subject (user will be used throughout, but it includes subjects that may not be the direct user of the device). The device 100 can alternatively be in the incorporated into an accessory article such as a wrist watch, phone, phone case, waist belt, sweat bands, or any other suitable accessory article for placement and securement in direct contact with a portion of a user. Additionally, the device 100 can be incorporated into other devices such a smart phone, a computer, a door lock, a security entrance, a door panel, or any other device where confirmation of a user's presence or identity of a user is desirable. The device 100 can be used with an optional output device, such as a smartphone (as shown), a smart watch, computer, mobile phone, tablet, a generic electronic processing and displaying unit, cloud storage, or a remote data repository via a cellular network or wireless Internet connection.

The device 100 includes an optical photodetector 110 and optical emitters 120, 140. In general, the device 100 uses two or more low-power lasers, light emitting diodes (LEDs) or quasi-monochromatic light sources as optical emitters 120, 140 and low-noise photodetecting electronics, as optical photodetectors 110, to determine the optical absorption of chromophores, such as water, hemoglobin in its multiple forms, including oxyhemoglobin ($HbO_2$), deoxyhemoglobin (HHb), oxymyoglobin, deoxymyoglobin, cytochrome c, lipids, melanins, lactate, glucose, myoglobin (including myoglobin at least one of oxymyoglobin, deoxymyoglobin, and total myoglobin) or metabolites. The metabolites can include at least one of lactate and lactic acid. Cytochrome c can be used, for example, to track muscle adaptation to training. In another example, the device 100 can use a broad-spectrum optical source, such as a light emitter 120, and a photodetector, such as the optical photodetector 110, that is sensitive to the spectral components of light, such as a spectrometer, or a charge-coupled device (CCD) or other linear photodetector coupled with near-infrared optical filters. As known to those skilled in the art, photodetectors 110 and light emitters 120 and 140 may be interchangeable without loss of generality. Also, multiple light emitters and light detectors can be used.

The optical-electronic device 100 can be operable to to include a sensor (not shown) operable to measure photoplethysmography (PPT) of the user. The sensor can include a corresponding optical emitter (not shown) and a corresponding optical photodetector (not shown). The device 100 can also include a second sensor (not shown) operable to measure electrocardiography (EKG) and derived systolic time intervals (STI) of the user. The second sensor can include a corresponding first electrode (not shown) and a corresponding second electrode (not shown). The optical-electronic device 100 can optionally include a processor that is operable to analyze data generated by the device 100 to determine a cardiac response to exercise and the supply, arteriovenous difference, utilization of oxygen by the muscle tissue and hydration of the muscular tissue. In other examples, the processor can be a part of a larger device and the optical-electronic device 100.

The device 100 can include a power supply, such as a battery, to supply power to the sensors and other components in the device 100. In one example, the device 100 has a skin contact area of 3.5"×2". In another example, the device 100 has a skin contact area of 35 mm×35 mm. The present technology can be implemented in a package that is just large enough to accommodate the desired spacing between the at least one emitter and the at least one detector.

In at least one example, the processor is operable to determine biological indicators, including, but not limited to a relative percentage, a saturation level, an absolute concentration, a rate of change, an index relative to a training threshold, and a threshold. In other cases, the processor is operable to determine perfusion characteristics such as pulsatile rhythm, blood volume, vascular tone, muscle tone, and angiogenesis from total hemoglobin and water measurements.

In at least one example, the processor is operable to discriminate between biological indicators and non-biological indicators. The processor is at least first operable to determine the presence of biological tissue. As indicated above, the issue can be human skin, mammalian skin or plant tissue, such as vegetables, legumes or fruits. In other examples, the tissue can be a particular type of tissue such as muscle tissue and epithelial tissue. When the presence of tissue is detected, the device can be operable to launch an activity. For example, the activity can be initiating data collection, unlocking an electronic device, transmitting data to a remote location, or other activity that can be used by an electronic device on which the sensors are located or a remote electronic device. In one example, if it is determined that the device 100 is in contact with a tissue of the user, the photodetector 110 will initiate data collection. The data collection can be based upon the desired characteristics that are being measured. The collection of data can, for example, be raw analog to digital conversion light counts corresponding to luminous radiations backscattered from the chromophores in a tissue of a user or in non-tissue material. From the collected data, an absolute level of the oxygenated hemoglobin concentration (HbO$_2$) and reduced hemoglobin (HHb), and corresponding total hemoglobin concentration, hemoglobin index and hydration index, can be calculated that enables the oxygenation/saturation of a tissue to be established, among other determinations as described herein. Other physiological traits of the user can be observed from the collected data such as, for example, the cadence, pace, and heart rate. If, however, it is determined that the device 100 is in contact with a non-tissue material, the photodetector 110 will not make measurements and device 100 could, for example, alert the user to check device placement. The determination can be made by a processor of the device 100, which contains optical data indicative of tissues of one or more users and non-tissue materials.

Figure 2A:
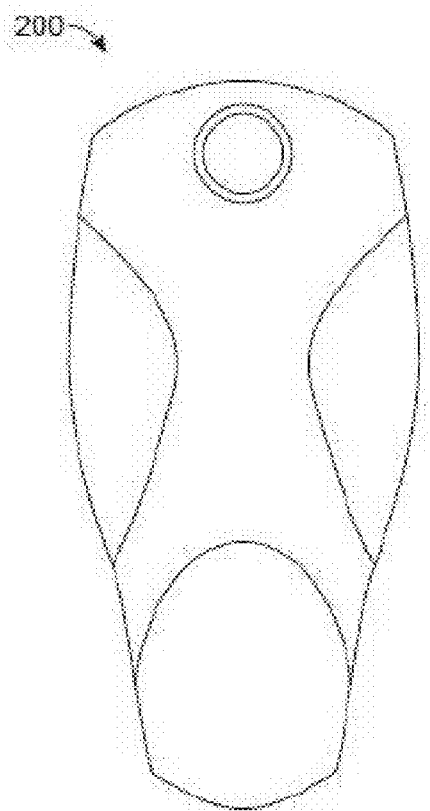
FIG. 2A is a schematic diagram of a front of a non-invasive optical-electronic device according to the present disclosure.
Figure 2B:
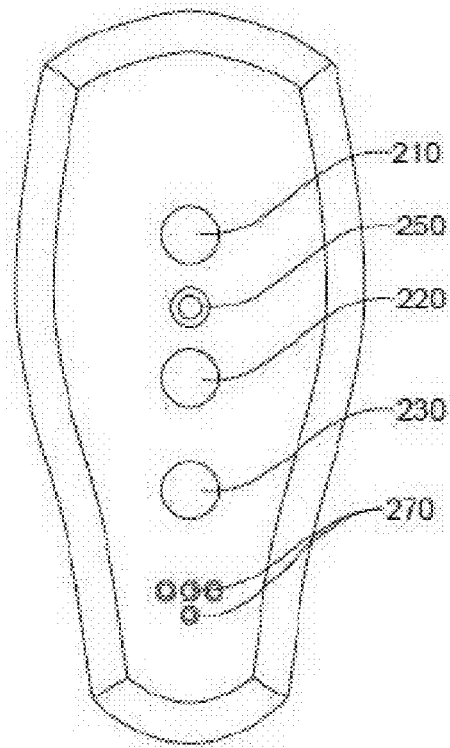
FIG. 2B is a schematic diagram of the back of a non-invasive optical-electronic device according to the present disclosure.
Figure 2C:
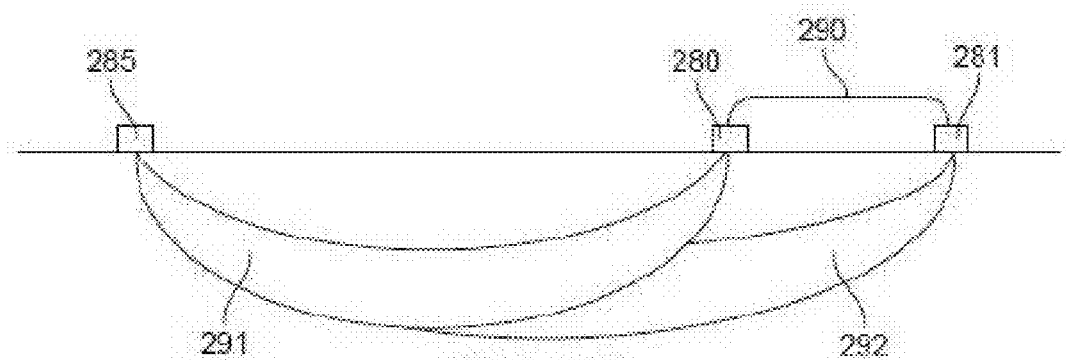
FIG. 2C is a schematic diagram of a Near-InfraRed Spectroscopy (NIRS) sensor that is included on a non-invasive optical-electronic device according to the present disclosure.

FIGS. 2A-2C illustrates a non-invasive optical-electronic device 200, according to an alternative example of the present disclosure. As mentioned above, the optical-electronic device can be incorporated into another device or article of clothing. The device 200 can be operable to be worn on a limb of a user as described above with respect to device 100. In at least one example, the device 200 can be optimized to a given limb for increased accuracy. In other examples, the device 200 can be optimized based on the size, gender, or age of the user. In still other examples, a variety of the above optimizations can be implemented for a given device. FIG. 2A illustrates the front of the optical-electronic device. FIG. 2B illustrates the back of the optical-electronic device, including emitters 220, 230, 250 and photodetector 210. The device 200 also includes data and charging contacts 270. In at least one example, the data and charging contacts 270 can be used to electrically detect if the sensor is making contact with the skin of a user. The presence of multiple emitters 220, 230, 250 on the optical-electronic device allows for spatially-resolved data gathering in real-time. The optical-electronic device 200 can be operable to determine the optical absorption of chromophores, such as water, hemoglobin in its multiple forms, including oxyhemoglobin (HbO$_2$), deoxyhemoglobin (HHb), oxymyoglobin, deoxymyoglobin, cytochrome c, lipids, melanins, lactate, glucose, or metabolites.

FIG. 2C illustrates a NIRS sensor that can be included on the non-invasive optical-electronic device 200, according to an example of the disclosure. As shown in FIG. 2C, the NIRS sensor includes light emitters 280 and 281 which emit light that is scattered and partially absorbed by the tissue. Each emitter 280, 281 can be operable to emit a single wavelength of light or a single range of wavelengths. In at least one example, each emitter 280, 281 can be operable to emit at least three wavelengths of light or at least three ranges of wavelengths. Each emitter 280, 281 can include one or more light emitting diodes (LEDs). Each emitter 280, 281 can include a low-powered laser, LED, or a quasi-monochromatic light source, or any combination thereof. Each emitter 280, 281 can also include a light filter.

A fraction of the light emitted by emitters 280 and 281 is detected by photodetector 285, as illustrated by the parabolic or "banana shaped" light arcs 291 and 292. As the symmetry of the light arcs indicate, the direction of light propagation does not matter. That is, emitter and photodetector locations are interchangeable and, hence, photodetectors could be replaced with light emitters, and vice-versa. Emitters 280, 281, are separated by a known distance 290 and produce a signal that is later detected at photodetector 285. The detected signal is used to estimate the effective attenuation and absorption coefficients of the underlying tissue as described later in FIG. 6, for example at blocks 640 and 650. In at least one example, the known distance 290 is 12 mm. In at least one example, the known distance 290 is 15 mm. In at least one example, the known distance 290 is 27 mm.

In other examples, the known distance can be selected based on a variety of factors, which can include the wavelength of the light, the tissue involved, the body mass index of the user or the age of the user.

The optical-electronic device 200 disclosed herein can have different numbers of emitters and photodetectors without departing from the principles of the present disclosure. Further, the emitters and photodetectors can be interchanged without departing from the principles of the present disclosure. Additionally, the wavelengths produced by the LEDs can be the same for each emitter or can be different.

In at least one example, the device 200 is used for the monitoring of physiological parameters of a user during a physical activity or routine. Use of the device 200 is particularly relevant in endurance type sports, such as running, cycling, multi-sport competition, rowing, but can also be used in other physical activities. The device 200 can be operable to wirelessly measure real-time muscle parameters during physical exercise. The device 200 can be secured to a selected muscle group of the user, such as the leg muscles of the vastus lateralis or gastrocnemius, which are primary muscle groups of running and cycling.

Figure 3:
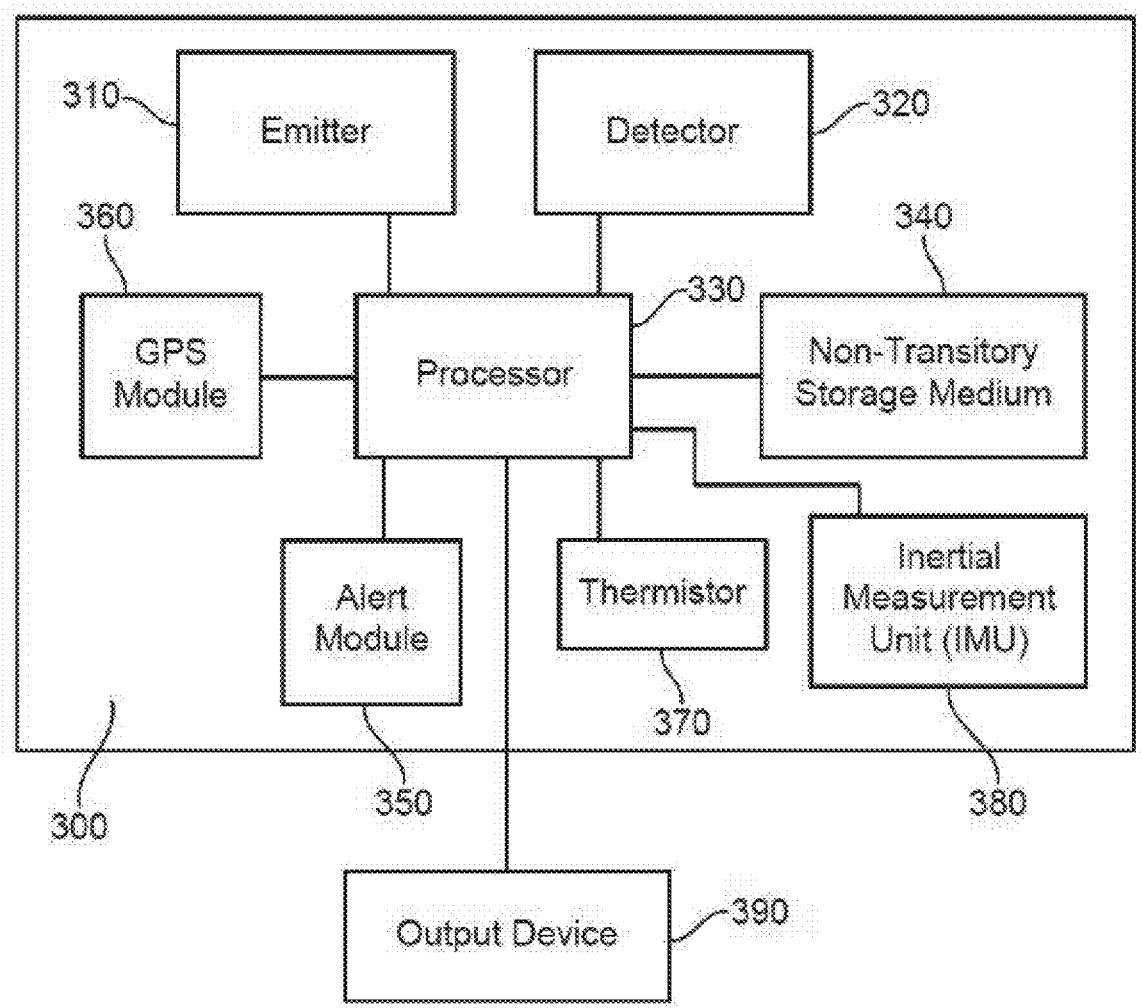
FIG. 3 illustrates the components of an optical-electronic device according to the present disclosure.

FIG. 3 illustrates the components of an optical-electronic device 300 according to an example of the present disclosure. As shown in FIG. 3, the optical-electronic device includes one or more emitters 310 and one or more photodetectors 320, which are coupled to a processor 330. The processor 330 is coupled to a non-transitory storage medium 340. The device 300 is coupled to an output device 390.

The one or more emitters 310 delivers light to the tissue and the one or more photodetectors 320 collect the optically attenuated signal that is back-scattered from the tissue. In at least one example, the one or more emitters 310 can be operable to emit at least three separate wavelengths of light. In another example, the one or more emitters 310 can be operable to emit at least three separate bands or ranges of wavelengths. In at least one example, the one or more emitters 310 can include one or more light emitting diodes (LEDs). The one or more emitters 310 can also include a light filter. The one or more emitters 310 can include a low-powered laser, LED, a quasi-monochromatic light source, or any combination thereof. The one or more emitters 310 can emit light ranging from infrared to ultraviolet light. As indicated above, the present disclosure uses NIRS as a primary example and the other types of light can be implemented in other examples and the description as it relates to NIRS does not limit the present disclosure in any way to prevent the use of the other wavelengths of light. In another example, the one or more emitters 310 emit light in the range from 600 nanometers to about 1100 nanometers, a range that is transmitted relatively well by tissue but which includes significant absorption by hemoglobin in the lower range and by water in the higher range, allowing improved detection of these chromophores.

The data generated by the one or more photodetectors 320 can be processed by the processor 330, such as a computer processor, according to instructions stored in the non-transitory storage medium 340 coupled to the processor. The processed data can be communicated to the output device 390 for storage or display to a user. The displayed processed data can be manipulated by the user using control buttons or touch screen controls on the output device 390.

The optical-electronic device 300 can include an alert module 350 operable to generate an alert. The processor 330 can send the alert to the output device 390 or the alert module 350 can send the alert directly to the output device 390. In at least one example, the optical-electronic device 300 can be configured so that the processor 330 is capable of sending an alert to the output device 390 without the device including an alert module 350.

The alert can provide notice to a user, via a speaker or display on the output device 390, of a change in biological indicator conditions or other parameter being monitored by the device 300, or the alert can be used to provide an updated biological indicator level to a user. In at least one example, the alert can be manifested as an auditory signal, a visual signal, a vibratory signal, or combinations thereof. In at least one example, an alert can be sent by the processor 330 when a predetermined biological indicator event occurs during a physical activity. In at least one example, an alert can be sent by the processor 330 when a non-biological indicator event, obtained for example from a non-tissue material, occurs during a physical activity or that the optical-electronic device 300 has not been in contact with the user for a predefined period of time.

In at least one example, the optical-electronic device 300 can include a Global Positioning System (GPS) module 360 capable of determining geographic position and tagging the biological indicator data with location-specific information. The optical-electronic device 300 can also include a thermistor 370 and an inertial measurement unit (IMU) 380. The inertial measurement unit (IMU) 380 can be used to measure, for example, gait performance of a runner or pedal kinematics of a cyclist, as well as physiological parameters of a user during a physical activity or routine. The thermistor 370 and inertial measurement unit (IMU) 380 can also serve as independent sensors capable of independently measuring parameters of physiological threshold. The thermistor 370 and inertial measurement unit (IMU) 380 can also be used in further algorithms to process or filter the optical signal.

Figure 4A:
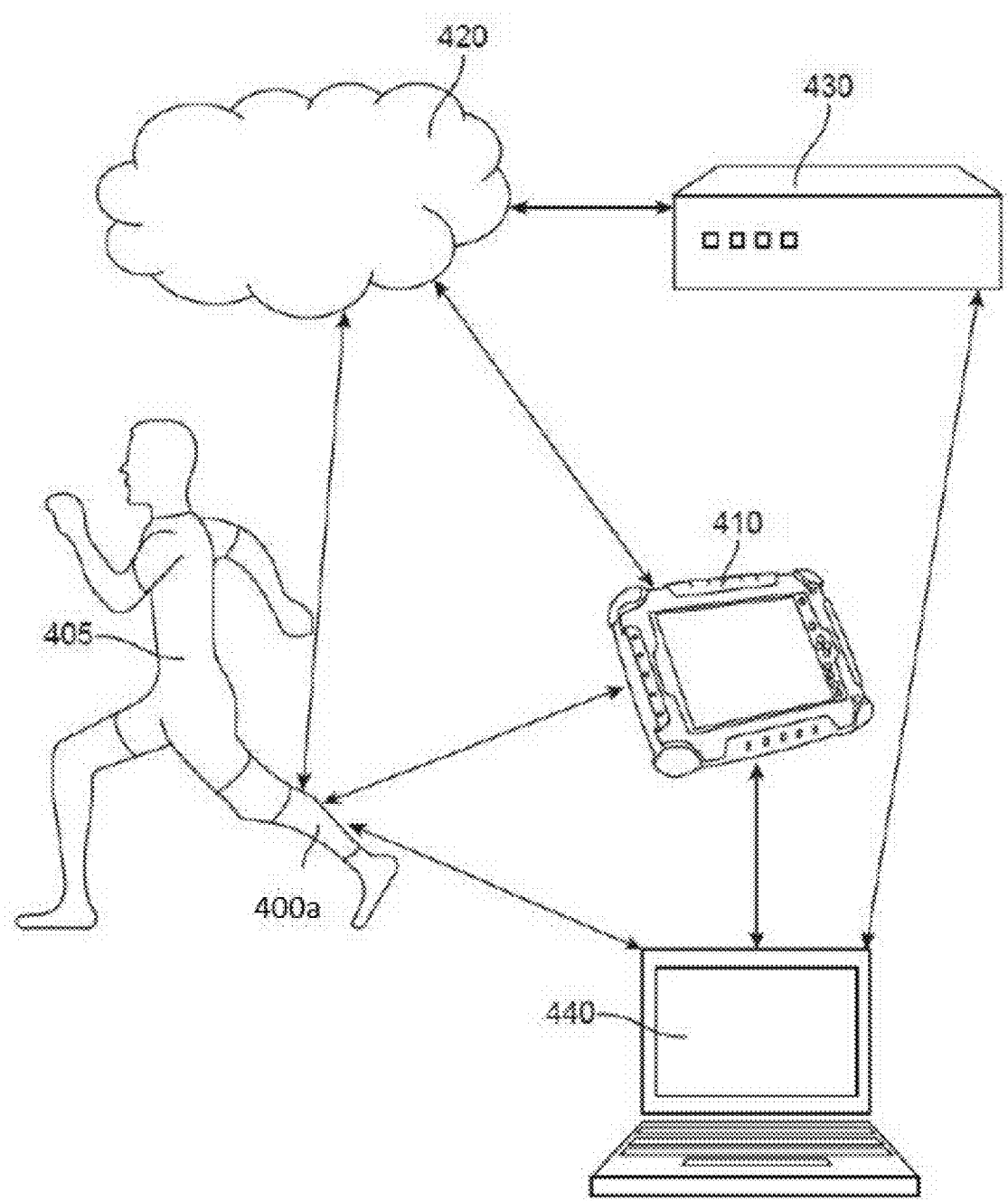
FIG. 4A illustrates an environment within which the non-invasive optical-electronic device can be implemented, according to the present disclosure.

FIG. 4A illustrates one example of an environment within which the non-invasive optical-electronic device 400a can be implemented, according to an example of the present disclosure. As shown in FIG. 4A, the optical-electronic device 400a is worn by a user to determine biological indicator levels during a physical activity or routine. The optical-electronic device 400a is depicted as being worn on the calf of a user 405; however, the optical-electronic device 400 can be worn on any portion of the user suitable for monitoring biological indicator levels. The device 400a can be used with an output device 410, such as a smartphone (as shown), a smart watch, computer, mobile phone, tablet, a generic electronic processing and displaying unit, cloud storage, or a remote data repository via a cellular network or wireless Internet connection.

As shown in FIG. 4A, the optical-electronic device 400a, communicates with an output device 410a so that data collected by the optical-electronic device 400a is displayed or transferred to the output device 410 for communication of real-time biological indicator data to the user 405a. In FIG. 4A, the optical-electronic device 400a is incorporated in a calf sleeve for direct contact with the calf of a user. In at least one example, an alert can be communicated from the device 400 to the output device 410 so that the user 405 can be notified of a biological indicator event. In at least one example, an alert can be communicated from the device 400a to the output device 410 so that the user 405 can be notified of a non-biological indicator event or that the optical-electronic device 400 has not been in contact with the user for a predefined period of time. Communication between the device 400a and the output device 410 can be via a wireless technology, such as BLUETOOTH®, infrared technology, or radio technology, or can be through a wired connection. Transfer of data between the optical-electronic device 400 and the output device 410 can also be via removable storage media, such as a secure digital (SD) card. In at least one example, a generic display unit can be substituted for the output device 410.

The optical-electronic device 400a also communicates with a personal computing device 440 or other device capable of storing or displaying user-specific biological indicator data. The personal computing device 440 can include a desktop computer, laptop computer, tablet, smartphone, smart watch, or other similar device. Communication between the device 400 and the personal computing device 440 can be via a wireless technology, such as BLUETOOTH®, infrared technology, or radio technology. In other examples, the communication between the device 400 and the personal computing device 440 can be through a wired or other physical connection. Transfer of data between the optical-electronic device 400 and the personal computing device 440 can also be via removable storage media, such as an SD card.

The output device 410 can communicate with a server 430 via a network 420, allowing transfer of user-specific biological indicator data to the server 430. The output device 410 can also communicate user-specific biological indicator data to cloud-based computer services or cloud-based data clusters via the network 420. The output device 410 can also synchronize user-specific biological indicator data with a personal computing device 440 or other device capable of storing or displaying user-specific biological indicator data. The output device 410 can also synchronize user-specific biological indicator data with a personal computing device 440 or other device capable of both storing and displaying user-specific biological indicator data. Alternatively, the personal computing device 440 can receive data from a server 430 or cloud-based computing service via the network 420.

The personal computing device 440 can communicate with a server 430 via a network 420, allowing the transfer of user-specific biological indicator data to the server 430. The personal computing device 440 can also communicate user-specific biological indicator data to cloud-based computer services or cloud-based data clusters via the network 420. The personal computing device 440 can also synchronize user-specific biological indicator data with the output device 410 or other device capable of storing or displaying user-specific biological indicator data.

The optical-electronic device 400a can also directly communicate data via the network 420 to a server 430 or cloud-based computing and data storage service. In at least one example, the device 400 can include a GPS module capable of communicating with GPS satellites (not shown) to obtain geographic position information.

The optical-electronic device 400a can be used by itself or in combination with other optical-electronic devices or biosensors. For example, the optical-electronic device 400a can be used in combination with heart rate (HR) biosensor devices, foot pod biosensor devices, and/or power meter biosensor devices. The optical-electronic device 400a can also be used in combination with ANT+™ wireless technology and devices that use ANT+™ wireless technology. The optical-electronic device 400a can be used to aggregate data collected by other biosensors including data collected by devices that use ANT+™ technologies. Aggregation of the biosensor data can be via a wireless technology, such as BLUETOOTH®, infrared technology, or radio technology, or can be through a wired connection.

The biosensor data aggregated by the optical-electronic device 400a can be communicated via a network 420 to a server 430 or to cloud-based computer services or cloud-based data clusters. The aggregated biosensor data can also be communicated from the optical-electronic device 400a to the output device 410 or personal computing device 440.

In at least one example, the optical-electronic device 400a can employ machine learning algorithms by comparing data collected in real-time with data for the same user previously stored on a server 430, output device 410, or in a cloud-based storage service. The machine learning algorithm can also be performed on or by any one of the output device 410, cloud-based computer service, server 430, or personal computing device 440, or any combination thereof.

Figure 4B:
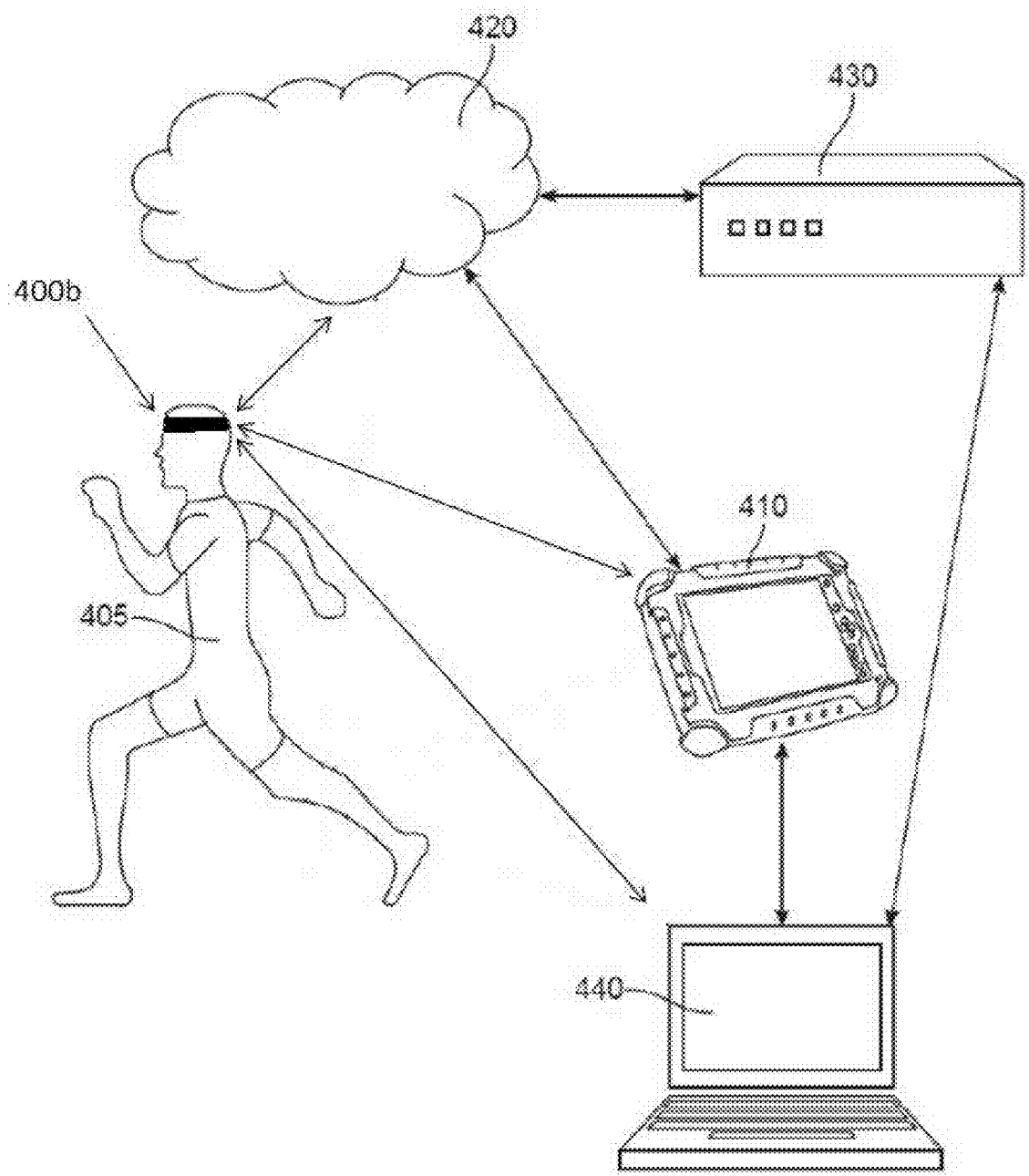
FIG. 4B illustrates another environment within which the non-invasive optical-electronic device can be implemented, according to the present disclosure.

FIG. 4B illustrates an example of an environment within which a non-invasive optical-electronic device 400b can be implemented, according to an example of the present disclosure. The optical-electronic device 400b is substantially similar to the optical-electronic device 400a except that the optical-electronic device 400b is incorporated in a head band for direct contact with the head of a user. While the illustration includes a headband, the present disclosure includes implementation in other devices or objects worn on the head such as eyewear, glasses, contact lenses, headphones, ear plugs, virtual reality devices. Other examples can be worn around the neck as well. In some implementations, the device can be operable to include a display device that allows for visual data to be displayed to the user.

Figure 4C:
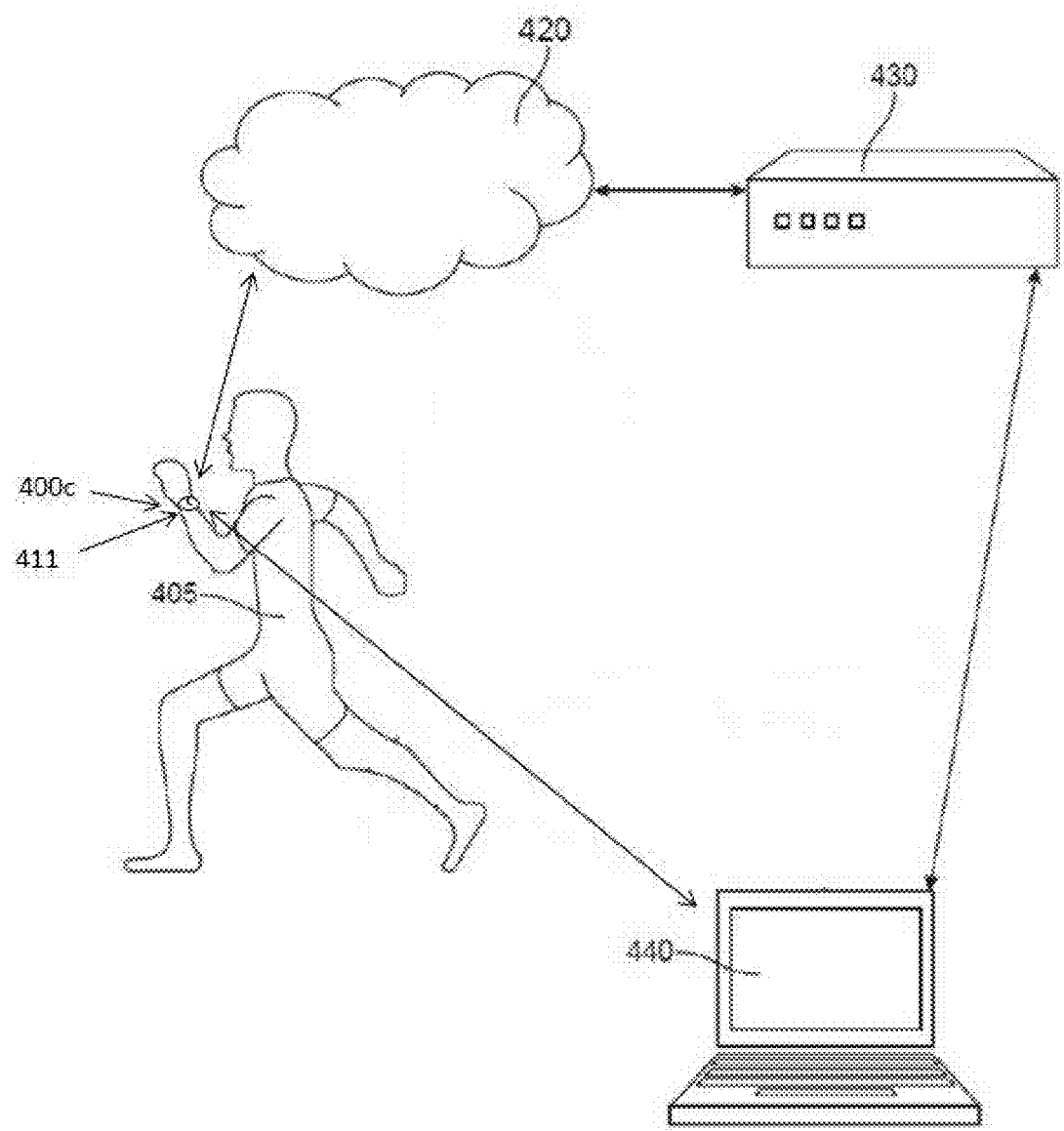
FIG. 4C illustrates another environment within which the non-invasive optical-electronic device can be implemented, according to the present disclosure.

FIG. 4C illustrates an example of an environment within which a non-invasive optical-electronic device 400c can be implemented, according to an example of the present disclosure. The optical-electronic device 400c is substantially similar to the optical-electronic device 400a and 400b except that the optical-electronic device 400b is incorporated in a wrist watch for direct contact with the wrist of a user. In at least one example, the wrist watch can be a smart watch, and can be an output device 411 which is substantially similar in function to output device 410. In other examples, the wrist watch can be implemented with a limited display and limited processing capability. In yet other examples, the optical-electronic device 400c can be incorporated in a wrist band.

According to the present disclosure, determination of the level of a biological indicator within tissue or blood vessels is achieved by calculating a relative match, or indices, between the spectral data received at the photodetector with a predetermined spectral data set of one or more chromophores corresponding to the biological indicator. In at least one example, the predetermined spectral data set corresponds to the signal spectra of specific analyses that can be readily obtained from the literature. See for example, Analyt. Biochem. Vol. 227, pp. 54-68 (1995). The relative match calculation is performed by calculating a projection of the spectral data set captured from a user in the direction of the predetermined spectral data set in order to calculate an index that reflects the proximity of the match. The spectral projection method can be used to calculate a relative percentage level of a biological indicator or, with proper calibration, can be used to calculate the absolute concentration of a biological indicator.

The spectral projection method of determining the level of a biological indicator can be implemented mathematically using the inner product method which will be explained, by way of example, using the TOI as the biological indicator of interest. TOI is the ratio of the oxygenated hemoglobin ($HbO_2$) to total hemoglobin (tHb), where total hemoglobin (tHb) is equal to the combined concentrations of the oxygenated hemoglobin ($HbO_2$) and the chromophore deoxygenated hemoglobin (HHb):

TOI=[HbO$_2$]/[tHb] or TOI %=100*([HbO$_2$]/[tHb]), where [THb]=[HbO$_2$]+[HHb].

TOI, as used herein, includes the more specific parameter, SmO2, which is the muscle oxygen saturation. SmO2 can also be the tissue oxygen saturation determined from optical measurements of muscle tissue. Both oxygenated hemoglobin (HbO2) and deoxygenated hemoglobin (HHb) are chromophores for which a spectral data set can be predetermined. The notation O(D) can be used to denote the predetermined spectral data for oxyhemoglobin (deoxyhemoglobin) at the same wavelengths for which the spectral data set for a user was measured at the photodetector, and U can be used to denote the measured data set, including an effective attenuation ($\mu_{eff}$) or an effective absorption coefficient ($\mu_a$). The inner product method of calculating the spectral projection can be calculated according to different mathematical methods, including, but not limited to, a direction cosine method, vector projection method, and a pseudo-inverse projection method.

Direction Cosine Method:

$$TOI = \frac{\langle U, O \rangle}{\left\langle U, O + D\sqrt{\frac{\langle O, O \rangle}{\langle D, D \rangle}} \right\rangle},$$

Vector Projection Method:

$$TOI = \frac{\langle U, O \rangle}{\left\langle U, O + D\frac{\langle O, O \rangle}{\langle D, D \rangle} \right\rangle},$$

Pseudo-Inverse Projection Method:

$$TOI = \frac{\left\langle U, O - \frac{\langle O, D \rangle}{\langle D, D \rangle} D \right\rangle}{\left\langle U, O\left[1 - \frac{\langle O, D \rangle}{\langle D, D \rangle}\right] + D\left[\frac{\langle O, O \rangle}{\langle D, D \rangle} - \frac{\langle O, D \rangle}{\langle D, D \rangle}\right] \right\rangle}.$$

All of these methods can be rewritten as $$TOI = \frac{\langle U, O - aD \rangle}{\langle U, O(1 - a) + D(b - a) \rangle}$$

where a and b are scalars defined as i) $a = 0,$
$b = \sqrt{\frac{\langle O, O \rangle}{\langle D, D \rangle}};$ ii) $a = 0,$
$b = \frac{\langle O, O \rangle}{\langle D, D \rangle};$
and iii) $a = \frac{\langle O, D \rangle}{\langle D, D \rangle}$
and
$b = \frac{\langle O, D \rangle}{\langle D, D \rangle}$ for the cosine, vector projection and pseudo-inverse methods, respectively.

Figure 5:
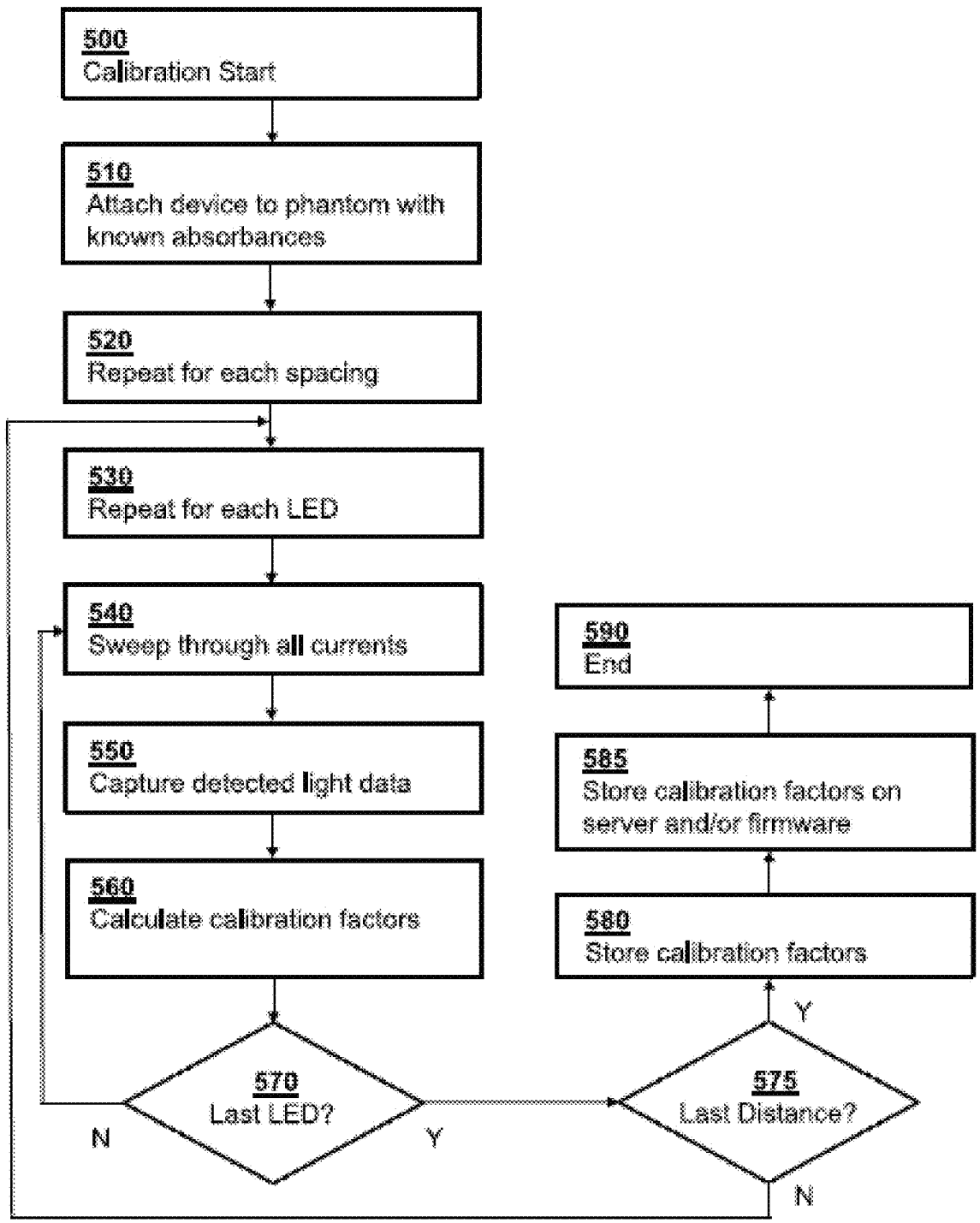
FIG. 5 is a flowchart describing an algorithm used to generate calibration factors used to convert detected light data into optical densities, according to an example of this disclosure.

Prior to calculating indices, calibration coefficients can be generated which allow the indices calculation to be corrected for the absorption properties of the tissue. FIG. 5 is a flowchart describing an algorithm used to generate the calibration coefficients that can be used, for example, by the projection indices algorithm.

Referring to FIG. 5, a flowchart is presented in accordance with an example. The example method shown in FIG. 5 is provided by way of an example, as there are a variety of ways to carry out the method. Each block shown in FIG. 5 represents one or more processes, methods, or subroutines, carried out in the example method shown in FIG. 5. Furthermore, the illustrated order of blocks is illustrative only and the order of the blocks can change according to the present disclosure. Additional blocks can be added or fewer blocks can be utilized, without departing from the present disclosure.

The example calibration method can begin at block 500. At block 510, any one of the above described the optical-electronic devices is attached to a phantom with known absorbances OD$_{jm}$. The above procedure is repeated for each spacing (m) at block 520 and for each LED (j) at block 530. At block 540, all currents (i) are swept. At block 550, light data D$_{ijm}$ are captured. The calibration factors are calculated at block 560, using the formula: C$_{ijm}$=10$^{ODjm}$/D$_{ijm}$. Block 570 determines whether the calibrations algorithm has been repeated for each LED emitter. If the calibration has not been performed for one or more LED emitters the blocks beginning with block 540 are repeated for the additional LED until all LEDs have been calibrated. Block 575 determines whether the calibration has been performed for all distances. If it is determined that calibration has not been performed for all distances, the blocks beginning with block 530 are repeated until the last LED and last distance has been calibrated, upon which the calibration factors are stored in block 580. Calibration factors C$_{ijm}$ are stored on a server and/or the firmware in block 585. The calibration algorithm is completed in block 590. The calibration factors stored according to the algorithm described in FIG. 5 can be used, for example, by the projection indices algorithm shown in FIG. 6.

Figure 6:
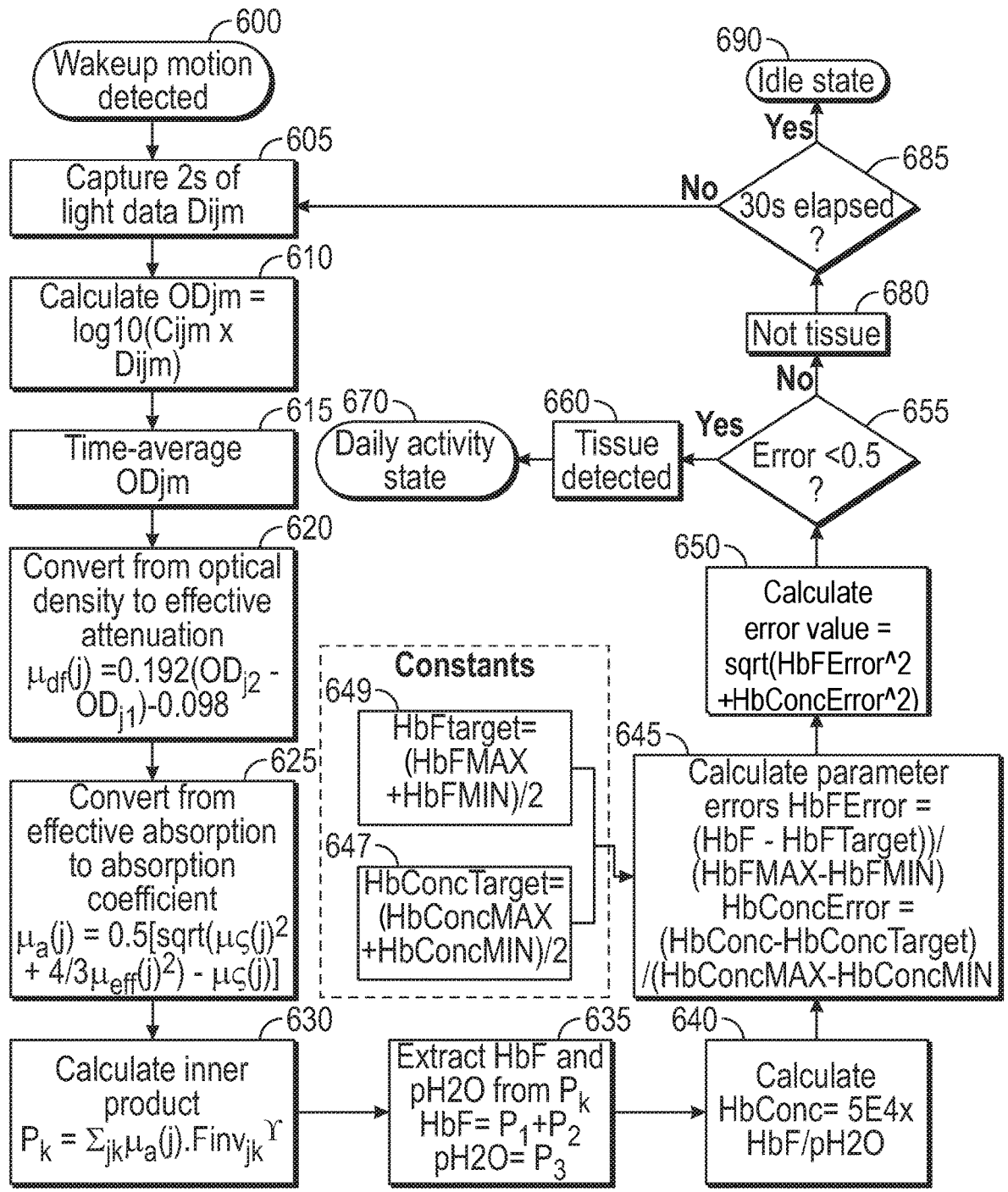
FIG. 6 is a flowchart describing a generic method of optical detection of a tissue of a user.

Referring to FIG. 6, a flowchart is presented in accordance with an example. The example method shown in FIG. 6 is provided by way of an example, as there are a variety of ways to carry out the method. Each block shown in FIG. 6 represents one or more processes, methods, or subroutines, carried out in the example method shown in FIG. 6. Furthermore, the illustrated order of blocks is illustrative only and the order of the blocks can change according to the present disclosure. Additional blocks can be added or fewer blocks can be utilized, without departing from the present disclosure.

FIG. 6 describes an exemplary method of optical detection of a tissue of a user and discrimination between the tissue of the user and non-tissue materials. The method can determine whether the device 100, 200, 300 is in contact with a tissue of a user or in contact with a non-tissue material. The device 100, 200, 300 starts from an off position, or, alternatively, a sleep mode. The example algorithm can begin at block 600. At block 600 the device 100, 200, 300 turns on (or activates) upon the detection of a wake motion of the device 100, 200, 300. The wake up motion can be for example a movement or motion of the device 100, 200, 300. Alternatively, the device can turn on incrementally or periodically, in block 600, in lieu of a motion or movement of the device 100, 200, 300. The period or increment of time can be any suitable periodic or incremental amount of time. For example, five seconds. In other examples, the device can send a signal to a coupled device. The coupled device can be a watch or smart phone that is coupled wired or wirelessly to the the device. The signal can be a hardware interrupt.

At block 605, the detected light data $D_{jm}$ is received by the device for a given current (i). Upon activating, the device 100, 200, 300 will generate and emit, using the corresponding optical emitters, radiation of at least three different wavelengths for irradiating a material surface which is in the path of the emitted radiation. In at least one example, at least one of the at least three different wavelengths can correspond to one of $HbO_2$, HHb or water. The device 100, 200, 300 will then detect, using the corresponding optical photodetector, the optically attenuated signal back-scattered from the material. The device 100, 200, 300 will detect data over a predetermined period of time at a predetermined sampling rate. In block 605, the predetermined timer period is two seconds. The device 100, 200, 300 can alternatively detect data over a time period ranging from 0.1 to 10 seconds, alternatively 0.5 to 5 seconds, and alternatively 1 to 3 seconds. The device can detect data over a predetermined sampling rate of 0.1 to 10 Hz, alternatively 0.5 to 10 Hz, alternatively, 1 to 10 Hz, alternatively, 2 to 8 Hz, alternatively, 4 to 6 Hz, and alternatively 5 Hz.

The detected light data are converted into optical densities for a given current i using the calibration factors $C_{jm}$, at block 610, using the equation: $OD_{jm}=\log_{10}(C_{ijm} \times D_{ijm})$. At block 615, a time-average of $OD_{jm}$ is determined. At block 620, the optical densities are converted to effective attenuations, using the equation: $\mu_{eff}(j)=0.192(OD_{j2}-OD_{j1})-0.098$. At block 625, the effective attenuations are converted to absorption coefficients, according to the equation:) $\mu_a(j)=0.5 [\sqrt{\mu_s'(j)^2+4/3\mu_{eff}(j)^2})-\mu_s'(j)]$ where $\mu_s'(j)$ is the reduced scattering coefficient for tissue being monitored, taken from, for example, from Applied Optics, Vol. 36, No. 1, pp. 386-396 (1997). The inner product is calculated at block 630, according to the equation: $P_k=\Sigma_j \mu_a(j) Finv_{jk}$, where $Finv_{jk}$ is the pseudo-inverse of the known absorption spectra of chromophores (k), wherein k=1 for oxyhemoglobin, k=2 for deoxyhemoglobin and k=3 for water, at wavelengths (j), and $\Sigma_j$ denotes summation over index (j). At block 635, the HbF and $pH_2O$ (that is, the percentage of water in the tissue) values are extracted from $P_k$, according to the equations $HbF=P_1+P_2$ and $pH_2O=P_3$. At block 640, the hemoglobin concentration index [HbConc] is determined, according to the formula $HbConc=(5e4 * HbF/pH_2O)$. At block 645, parameter errors are calculated, according to the following equations HbFError=(HbF-HbFTarget)/(HbFMAX-HbFMIN), and HbConcError=(HbConc-HbConcTarget)/(HbConcMAX-HbConcMIN). Constant values HbFTarget and HbConcTarget are given by HbFTarget=(HbFMAX+HbFMIN)/2 and HbConcTarget =(HbConcMAX+HbConcMIN)/2, as displayed in blocks 647 and 649, respectively. If the HbF is greater than a minimum threshold value and less than a maximum threshold value, and the HbConc is greater than a minimum threshold value and less than a maximum threshold value, then a determination that the photodetector is directed to a tissue of a user is made as described below, and further data collection is performed and the data is collected for use in exercise analysis. In at least one example, the hemoglobin concentration index minimum threshold value (HbConcMIN) is 4.47. In at least one example, the hemoglobin concentration index maximum threshold value (HbConcMAX) is 40.16. In at least one example, the HbF minimum threshold value (HbFMIN) is 2.30e-5. In at least one example, the HbF maximum threshold value (HbFMAX)) is 2.54e-4.

At block 650, an Error Value is calculated according to the equation: Error Value=sqrt(HbFError^2+HbConcError^2). At block 655, the error value is compared to a set error value of 0.5. If the error value obtained in block 650 is less than 0.5, a determination is made at block 660 that a tissue of a user is detected and subsequently enters a Daily Activity State, as shown in block 670. If the error value obtained in block 650 is greater than 0.5, a determination is made at block 680 that a non-tissue material is detected.

In block 670, the device 100, 200, 300 will continue to generate and emit, using the corresponding optical emitters, radiation of at least two different wavelengths until a tissue is no longer detected or until a predetermined period of time has passed as done in blocks 685 and 690, respectively.

In block 685, upon determination in block 680 that a non-tissue material, the method will repeat, starting at block 605, for an allotted amount of time. As shown in block 685, the allotted time can be a 30 second time period. The allotted time can be up to, for example, 5 seconds, alternatively 10 seconds, alternatively 15 seconds, alternatively 30 seconds, and alternatively 60 seconds. In block 690, if after the allotted time period no tissue has been detected, the device will enter an idle state. The idle state can be an off position or a sleep mode as described above or any other idle state which reduces power consumption.

In another example the error values HbConcError and HbFError are linearly transformed and translated before their Euclidian distance to the origin is calculated, wherein the translation is given by subtraction by the mean value of HbConc and HbF parameters measured from a set X of known tissue measurements, and the linear transformation is given by matrix multiplication of the vector [HbConcError HbFError] with $\Lambda^{-1/2}U^T$, wherein $\Lambda$ and U are the eigenvalue and eigenvector matrices of the covariance matrix of X.

As described above, the devices 100, 200, 300 can be used for the study of muscle tissue oxygenation during exercise. The application of the present technology is particularly relevant in endurance type sports, such as running, cycling, multisport competition, rowing, etc., but can also be successfully applied to other types of exercises and training methods. The devices 100, 200, 300 can be operable to wirelessly measure real-time muscle parameters during physical exercise. The devices 100, 200, 300 can be secured to a selected muscle group of the user, such as the leg muscles of the vastus lateralis or gastrocnemius, as described above (See FIG. 4A) which are primary muscle groups of running and cycling.

Muscle tissues increase their oxygen requirements during periods of increased stress (e.g. athletic activity). The more a muscle is being stressed the more oxygen is extracted from arterial blood to supply these needs. Therefore an appreciable desaturation of hemoglobin occurs in stressed muscles, which correlates with exercise intensity. At the same time, at rest and under steady-state exercise conditions, there is a balance between blood lactate production and its subsequent removal. As the muscles are stressed to greater and greater degrees more lactic acid is also produced as a byproduct. At a certain point (unique to each user) the body begins producing more lactic acid than it can remove. The LT refers to the intensity of exercise at which there is an abrupt increase in blood lactate levels above baseline. Coaches and trainers use the LT pace to generate training programs (frequently referred to as zone training) that are a combination of high volume low intensity, maximal steady-state, and supra-threshold interval workouts to improve athletic performance. LT training is one way to improve athletic performance of the user.

During an exercise routine, which can comprise, for example, running, cycling, or swimming stages, or any other stage of an exercise routine, the devices 100, 200, 300 can, as described above, determine whether the devices 100, 200, 300 are in contact with a tissue of a user as described above, in contact with a non-tissue material, or in contact with both, to determine whether to obtain data for exercise analysis. The optical-electronic devices 100, 200, 300, as disclosed herein, can also transmit a signal or an alert to an output device such as a user display or mobile device. One form of an alert can signal or flag the existence of non-tissue materials which interfere with the identification and/or determination of one or more biological indicators. The existence of non-tissue materials can be indicated by determining the relative match of a spectral data set representative of received light and the null space for a matrix containing the spectra representative of a predetermined data set of one or more chromophores, which is the set of vectors that will be mapped to 0 by the F matrix. As described at Step 650 of FIG. 6, the inner product is calculated as $P_k=\Sigma_j\mu_a(j)Finv_{jk}$, where $P_k$ are the projections due to analyte k, and Finv is the pseudo-inverse of matrix F containing the spectra of the analytes at wavelengths (j). The residual signal R is given by $R=\mu_a-P*F^T$, where T denotes the transpose and * denotes matrix multiplication. Accordingly, R represents the part of the detected signal that failed to project towards any of the analytes of interest. Under normal conditions, R remains low. However, under special conditions, such as when clothing interferes with the optical-electronic device, an abrupt increase in the modulus of R would be expected. When the modulus of R increases suddenly, or when it surpasses a pre-determined threshold, an alarm can be conveyed to the user. Accordingly, the optical-electronic device can be operable to generate a null-space or residual signal to flag the existence of non-tissue materials, including, but not limited to: tabletops, textiles, fabrics, plastics, polymeric materials, cellulosic materials, or other similar non-tissue materials.

The method described in FIG. 6 of using the device 100, 200, 300 can include placing the optical photodetector and optical emitters in contact with the tissue to be analyzed, and starting the measuring cycle by using an appropriate signal. The method can also include the step of emitting luminous radiations from the optical emitters at a given optical intensity and at least at three different wavelengths in the near-infrared spectrum, where at least one is correspondent to a water absorption peak, in particular 980 nm, for a localized illumination of the tissue. Further, the method can include detecting the optical intensity of the luminous radiations backscattered from the tissue using the optical photodetector at a set distance from the illuminated zone and transforming the backscattered radiation detected in low noise electric signal. The method can further include calculating the absolute concentrations of oxygenated and deoxygenated hemoglobin, according to the photon diffusion equation using the absorption coefficients previously calculated, and the step of calculating the absolute concentration of total hemoglobin as a sum of the oxygenated hemoglobin and deoxygenated hemoglobin concentrations and the oxygenation index of the tissue as the ratio of the oxygenated hemoglobin concentration over the total hemoglobin concentration.

Additionally, the method can include displaying the data on the electronic device. The steps for collecting, processing, analyzing, and calculating information from the photodetector can be implemented in computer programs using standard programming techniques. The program code is applied to data generated by the photodetector to perform the functions described herein and generate output information NIRS variables (e.g., physiological parameters). Each such computer program can be stored on the processor in the photodetector or machine readable storage medium (for example, CD ROM, hard drive, or flash drive) that when read by the processor or other computer machines can cause the processor in the photodetector to perform the analysis and control functions described herein.

In at least one example the tissue detection of block 660 signal can be further used to determine whether the device is in continuous contact with tissue, issuing an alarm whenever the device is determined to be out of contact with tissue for an allotted amount of time. The alarm can be visual or audible in nature, or any other suitable means for alarming the user. The allotted time can be for example, 5 seconds, alternatively 10 seconds, alternatively 15 seconds, alternatively 30 seconds, and alternatively 60 seconds. The allotted time can be, more particularly, 30 seconds.

In at least another example the tissue detection signal is further used to determine whether a specific user is trying to activate the device. Here, the user tissue data is first enrolled (measured) during an enrollment phase, in which multiple readings from multiple locations in the user body are captured, thus creating a new and personalized range of thresholds to be used. That is, a personalized set of HbFMIN, HbFMAX, HbConcMIN, HbConcMAX values. Then, during tissue detection the user-specific thresholds are used, resulting in a tissue detection function more specific for that user while also rejecting a fraction of other users and better rejecting non-tissue materials.

Experimental Results

To test the ability of the device 200 to discriminate between tissue of a user and non-tissue materials, tissue detection trials were performed using the device 200 on body parts of a user comprising tissue and non-tissue materials. In a first, a second and a third trial described below, data was obtained using the following procedure under room lighting of approximately 1 candela. First, the device 200 was placed in direct contact with a body part of a user. Optical data was collected for 60 seconds. After the 60 second period, the device 200 was moved to another body part or non-tissue material, depending on the trial, and optical data ($D_{ijm}$) was collected for 60 seconds. The period of data collection and transferring to another body part or non-tissue material was continued until all body parts and non-tissue materials were tested. After optical data was collected for the last non-tissue material, the data collected for all body parts and non-tissue materials were tabulated for comparison. Irradiation of the samples and data collection and analysis were performed as previously described.

In the first trial, using the device 200, tissue detection trials were performed, in the following order, on the left calf and left forearm of a user, as the tissue sources, and on a black lycra sleeve, a gray lycra sleeve, a ream of white paper, a dark wooden table, a light colored carpet, a phone LCD screen, a phone cover, a roll of toilet paper, a front portion of a heart rate monitor, and back portion of a heart rate monitor.

In the second trial, using the device 200, tissue detection trials were performed, in the following order, on the left calf of a user, a formica table top, a dry towel, a humid towel, and a wet towel, a lens of a pair of swim goggles, a dry lycra swimsuit, a wet lycra swimsuit, a rubber fin, a rubber swim cap, and a clear plastic bag containing a wet swimsuit therein.

In the third trial, using the device 200, tissue detection trials were performed, in the following order, on the left calf of a user, the right calf of the user, the right forearm of the user, the palm of the right hand of the user, a white laminate tabletop, the interior of a backpack, the interior of a canvas bag, a rubber shoe sole, a transparent water bottle having water therein, a foam headphone, and the wrapper of a food bar.

Figure 7A:
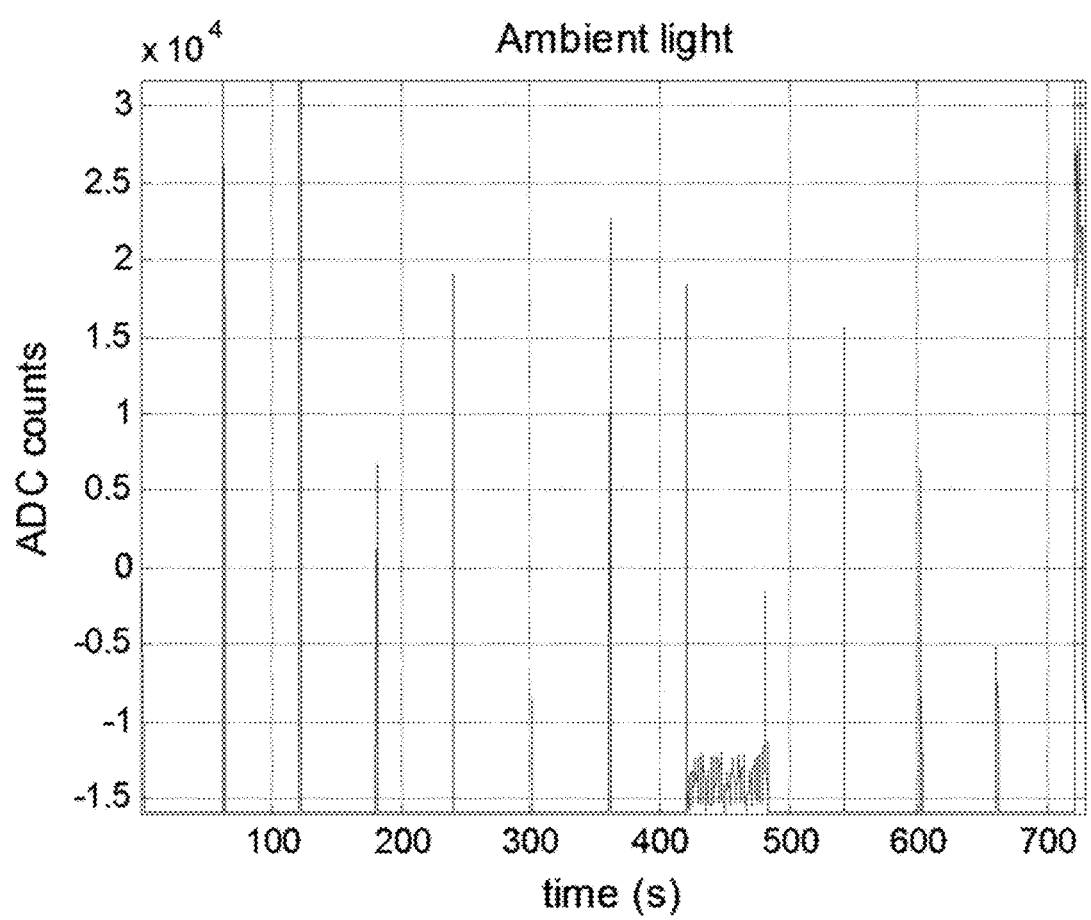
FIG. 7A is a graph displaying raw analog to digital conversion (ADC) ambient light counts corresponding to optical data detected, during a first trial, from tissues of a user and non-tissue materials.

FIG. 7A is a graph displaying raw ADC ambient light counts corresponding to optical data detected, during the first trial, from tissues of a user and non-tissue materials. Signal spikes correspond with the movement of the device 200 from one tissue to another, one tissue to a non-tissue material, or from one non-tissue material to another, since the photodetector gets exposed to ambient light during movement. The first signal spike corresponds to the movement of the device 200 from the left calf of a user to the left forearm of the user, the second spike corresponds to the movement of the device 200 from the left forearm of the user to a black lycra sleeve, the third spike corresponds to the movement of the device 200 from the black lycra sleeve to a gray lycra sleeve, the fourth spike corresponds to the movement of the device 200 from the gray lycra sleeve to a ream of white paper, the fifth spike corresponds to the movement of the device 200 from the ream of white paper to a dark wooden table, the sixth spike corresponds to the movement of the device 200 from the dark wooden table to a light-colored carpet, the seventh spike corresponds to the movement of the device 200 from the light-colored carpet to a phone LCD screen, the eighth spike corresponds to the movement of the device 200 from the phone LCD screen to a phone cover, the ninth spike corresponds to the movement of the device 200 from the phone cover to a roll of toilet paper, the tenth spike corresponds to the movement of the device 200 from the roll of toilet paper to a front portion of a heart rate monitor, and the eleventh spike corresponds to the movement of the device 100 from the front portion of a heart rate monitor to a back portion of a heart rate monitor.

Figure 7B:
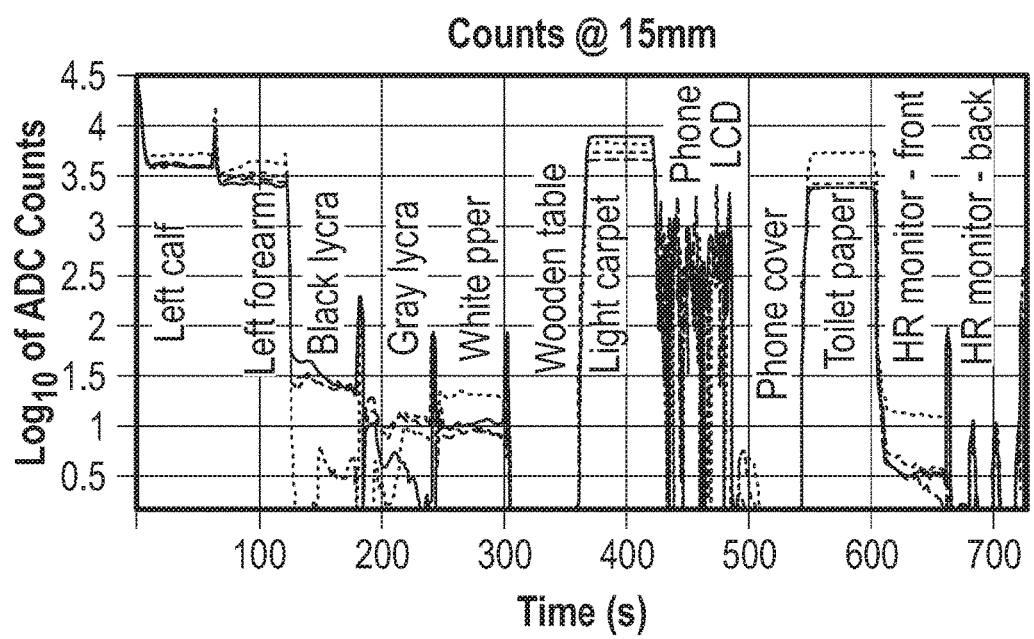
FIG. 7B is a graph displaying the common logarithm of the optical data ($D_{ijm}$ at a 15 mm LED to photodiode separation distance.

FIG. 7B is a graph displaying the common logarithm of the optical data ($D_{ijm}$) at an LED-to-photo detector spacing of 15 mm. The data was obtained when the first optical emitter and optical photodetector are separated by a distance of fifteen millimeters (mm) (7A) and the second optical emitter and optical photodetector are separated by a distance of 27 mm (7E). As indicated above, the spacing can be adjusted and is not considered limiting on the present disclosure. As with previous data, signal spikes correspond with the movement of the device 200 from one tissue to another, one tissue to a non-tissue material, or from one non-tissue material to another. From the obtained optical data, $\mu_a$ and $P_k(t)$ of each tissue and non-tissue material were calculated and HbF and HbConc were determined.

Figure 7C:
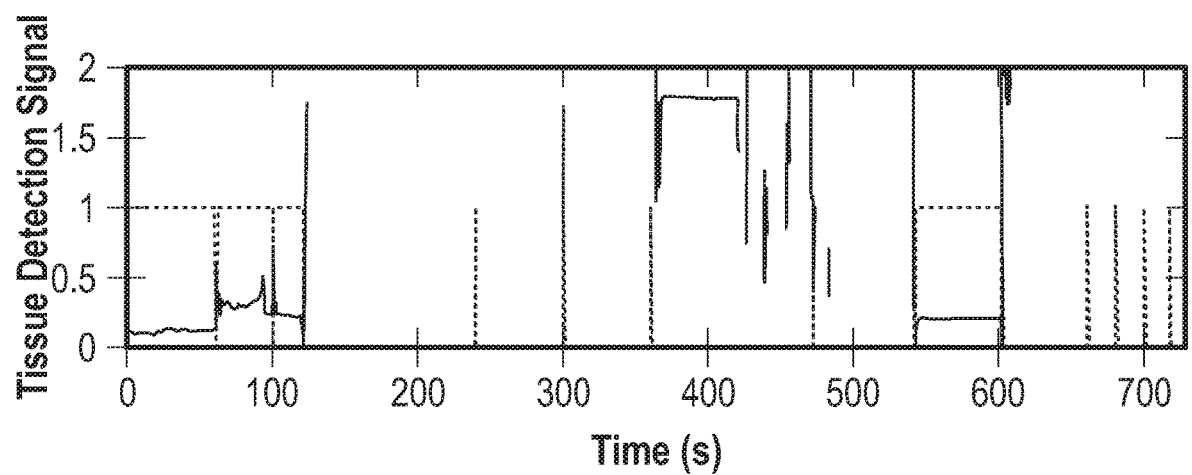
FIG. 7C is a graph displaying tissue detection signals derived from optical data detected during the first trial from the tissues of the user and the non-tissue materials.

FIG. 7C is a graph displaying tissue detection signals derived from optical data detected during the first trial from the tissues of the user and the non-tissue materials. As with previous data, signal spikes correspond with the movement of the device 200 from one tissue to another, one tissue to a non-tissue material, or from one non-tissue material to another. A horizontal line having a Tissue Detection Signal value of less than 0.5 corresponds to either a tissue or non-tissue material which is a false positive, as described above. A Tissue Detection signal of less than 0.5 corresponds to a tissue having a hemoglobin index value and a hemoglobin concentration value in a range as described in references to FIGS. 11 and 13 respectively.

Figure 7D:
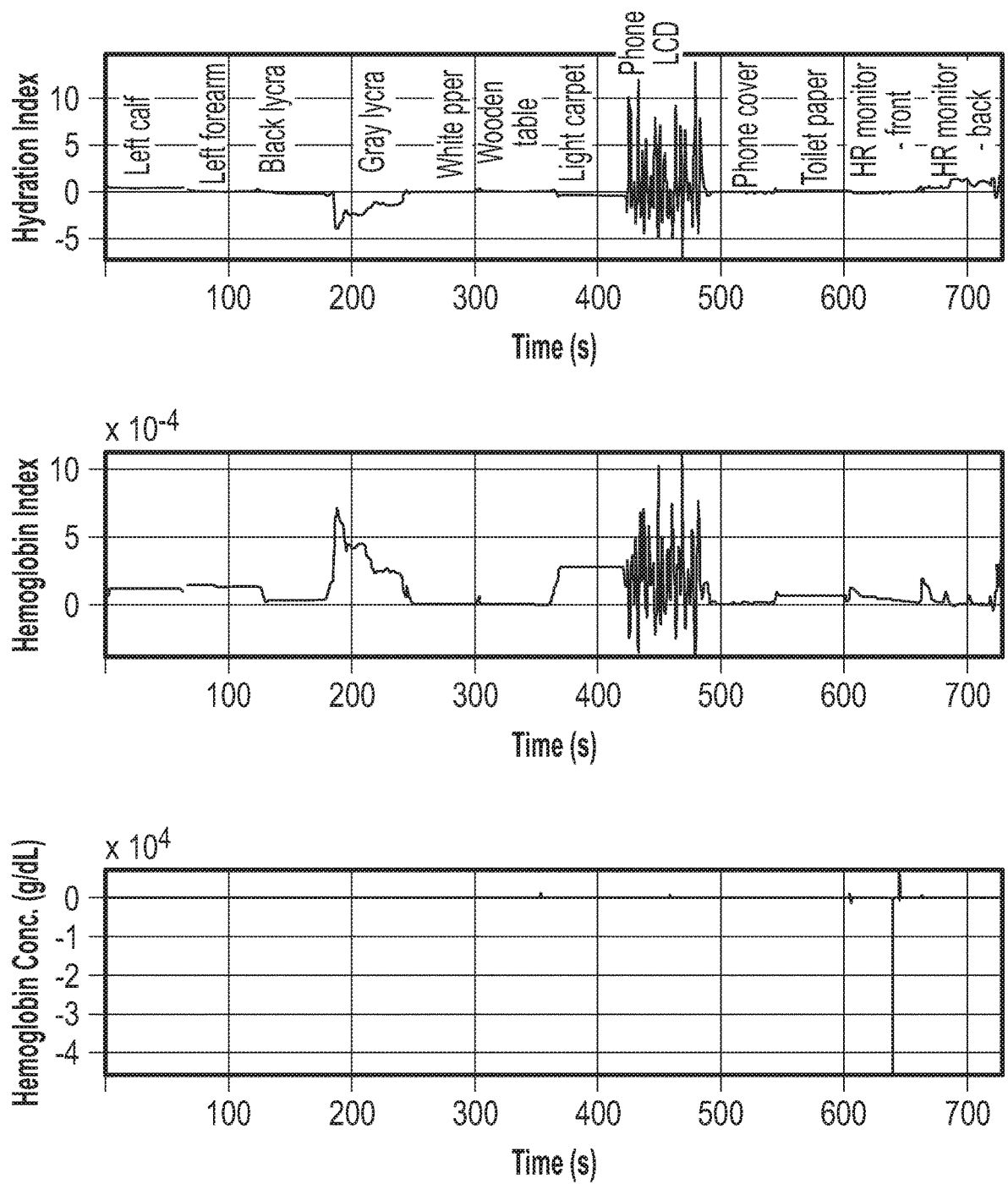
FIG. 7D is a graph displaying hydration indices (top), hemoglobin indices (middle), and hemoglobin concentration indices (bottom) derived from optical data detected during the first trial from the tissues of the user and the non-tissue materials.
Figure 11:
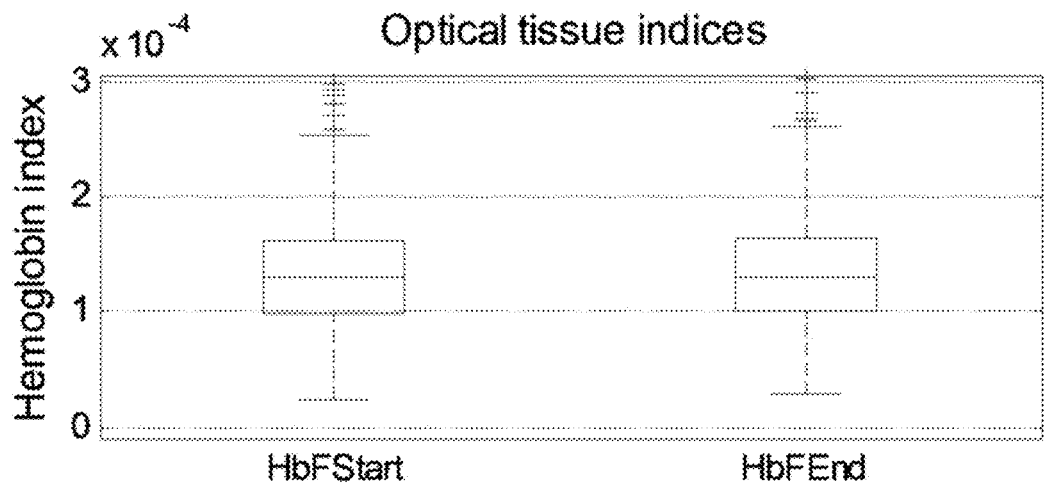
FIG. 11 is a graph displaying two ranges of hemoglobin index (y-axis) compiled from optical data of user profiles using an exemplary non-invasive optical tissue detection device according to the disclosure herein.
Figure 13:
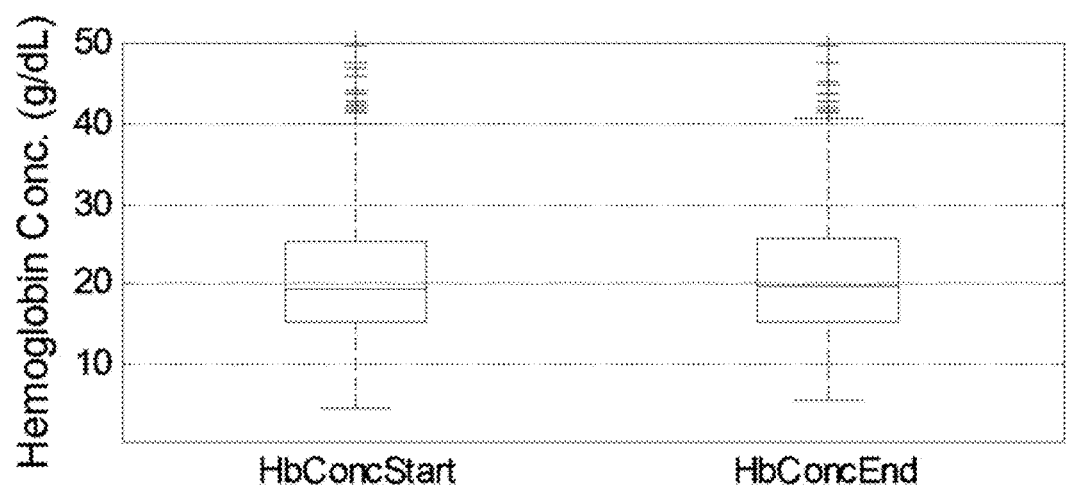
FIG. 13 is a graph displaying two ranges of hemoglobin concentration (y-axis) compiled from optical data of the user profiles using an exemplary non-invasive optical tissue detection device according to the disclosure herein.

FIG. 7D is a graph displaying hydration indices (top), hemoglobin indices (middle), and hemoglobin concentration indices (bottom) derived from optical data detected during the first trial from the tissues of the user and the non-tissue materials, showing that non-tissue materials generally have HbF and HbConc values that vary from those described by FIGS. 11 and 13.

Figure 7E:
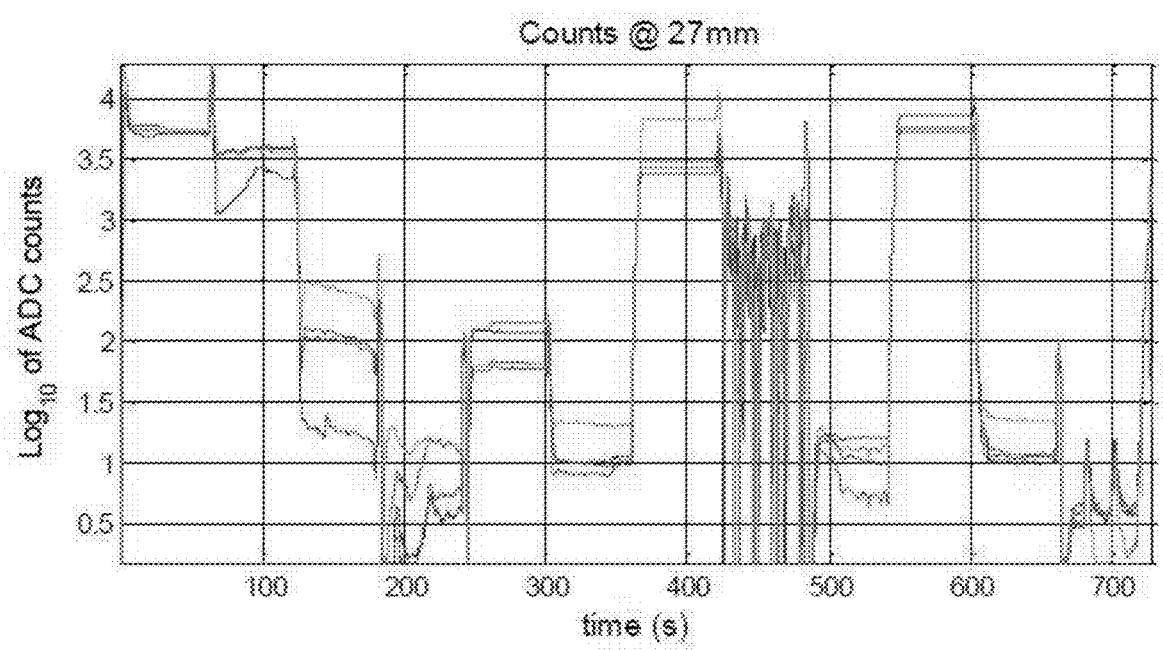
FIG. 7E is a graph displaying the common logarithm of the ADC counts corresponding to optical data detected from the tissues of the user and the non-tissue materials of the first trial at a 27 mm LED to photodiode separation distance.

FIG. 7E is a graph displaying the common logarithm of the ADC counts corresponding to optical data ($D_{ijm}$) detected from the tissues of the user and the non-tissue materials of the first trial, wherein the optical emitter and optical photodetector are separated by a distance of twenty-seven mm. As with previous data, signal spikes correspond with the movement of the device 200 from one tissue to another, one tissue to a non-tissue material, or from one non-tissue material to another.

Figure 8A:
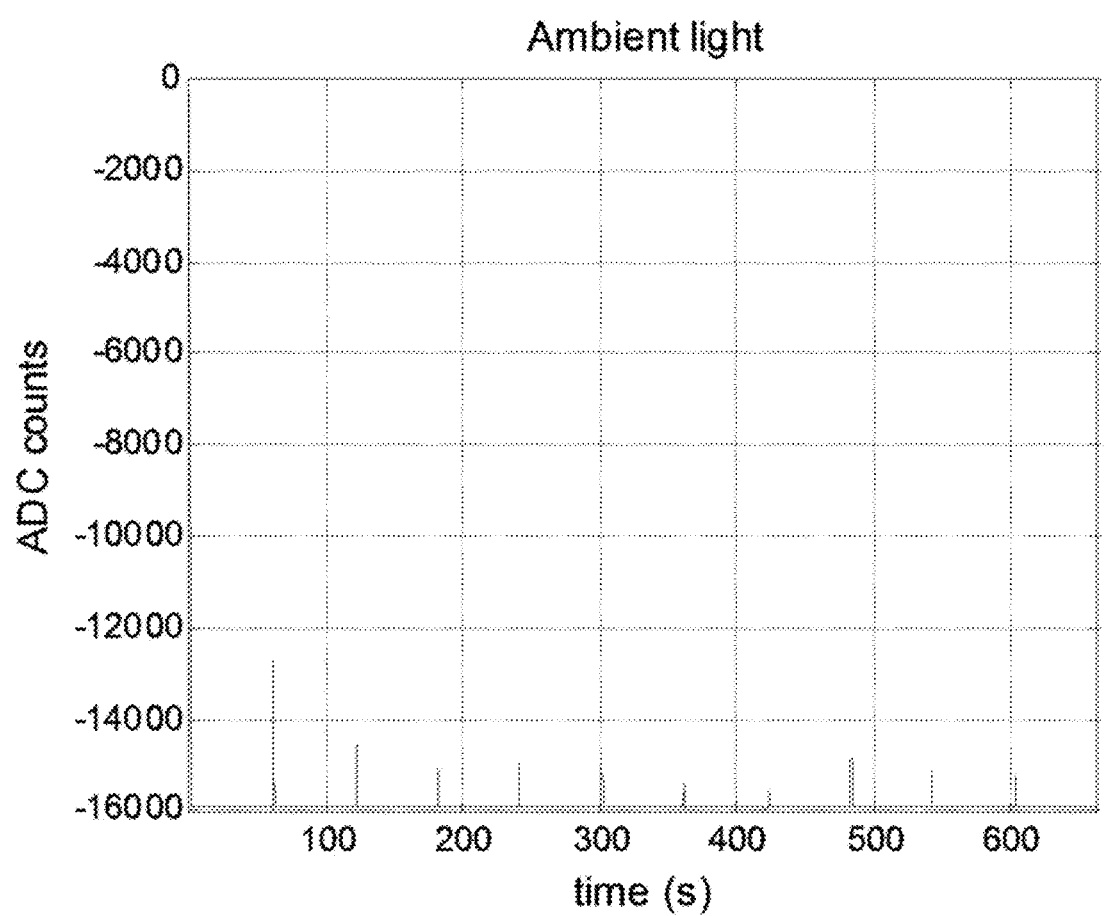
FIG. 8A is a graph displaying raw ADC ambient light counts corresponding to optical data detected during a second trial from tissues of a user and non-tissue materials.

FIG. 8A is a graph displaying raw ADC ambient light counts. Signal spikes correspond with the movement of the device 200 from one tissue to another, one tissue to a non-tissue material, or from one non-tissue material to another. The first signal spike corresponds to the movement of the device 200 from the left calf of a user to a formica tabletop, the second spike corresponds to the movement of the device 200 from the formica tabletop to a dry towel, the third spike corresponds to the movement of the device 200 from the dry towel to a damp towel, the fourth spike corresponds to the movement of the device 200 from the damp towel to a very wet towel, the fifth spike corresponds to the movement of the device 200 from the very wet towel to a lens of a pair of swim goggles, the sixth spike corresponds to the movement of the device 200 from the lens of a pair of swim goggles to a dry lycra swimsuit, the seventh spike corresponds to the movement of the device 200 from the dry lycra swimsuit to a wet lycra swimsuit, the eighth spike corresponds to the movement of the device 200 from the wet lycra swimsuit to a rubber fin, the ninth spike corresponds to the movement of the device 200 from the rubber fin to a rubber swim cap, and the tenth spike corresponds to the movement of the device 200 from the rubber swim cap to a plastic bag containing a wet swimsuit.

Figure 8B:
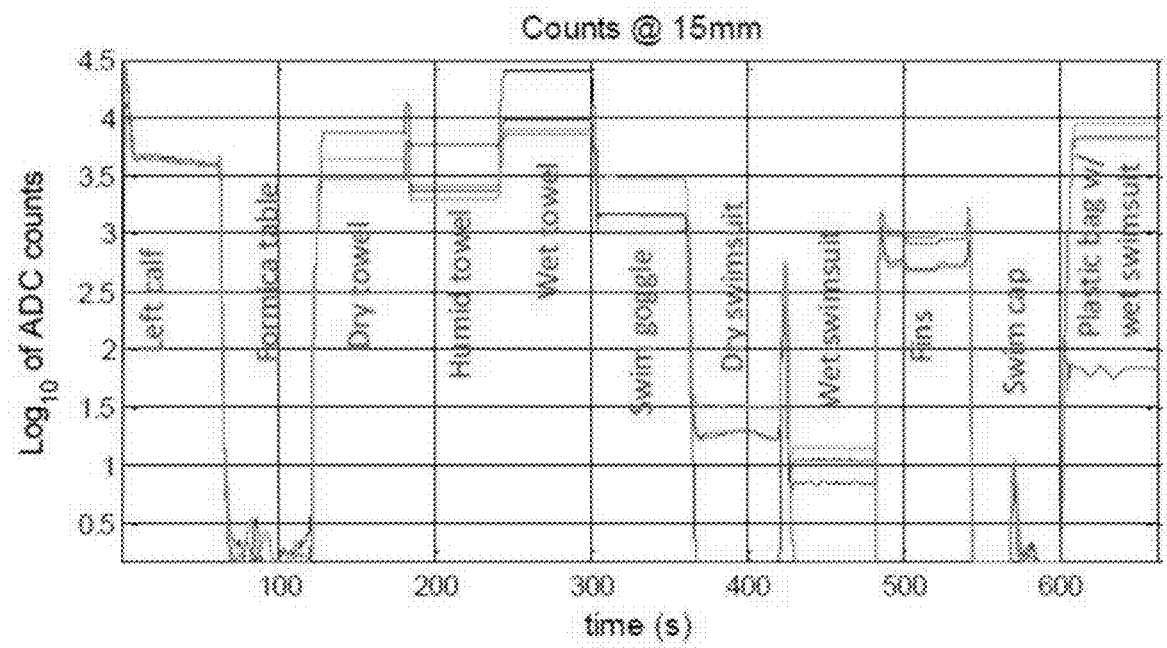
FIG. 8B is a graph displaying the common logarithm of the optical data ($D_{ijm}$) at a 15 mm LED to photodiode separation distance.

FIG. 8B is a graph displaying the common logarithm of the optical data ($D_{ijm}$). As with previous data, signal spikes correspond with the movement of the device 200 from one tissue to another, one tissue to a non-tissue material, or from one non-tissue material to another. From the obtained optical data, $\mu_a$ and $P_k(t)$ of each tissue and non-tissue material were calculated and HbF and HbConc were determined.

Figure 8C:
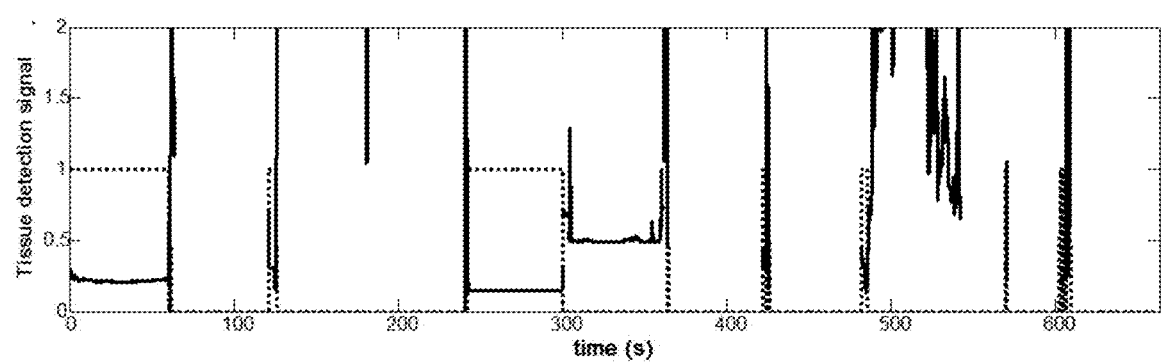
FIG. 8C is a graph displaying tissue detection signals derived from optical data detected during the second trial from the tissues of the user and the non-tissue materials.

FIG. 8C is a graph displaying tissue detection signals derived from optical data detected during the second trial from the tissues of the user and the non-tissue materials. As with previous data, signal spikes correspond with the movement of the device 200 from one tissue to another, one tissue to a non-tissue material, or from one non-tissue material to another.

Figure 8D:
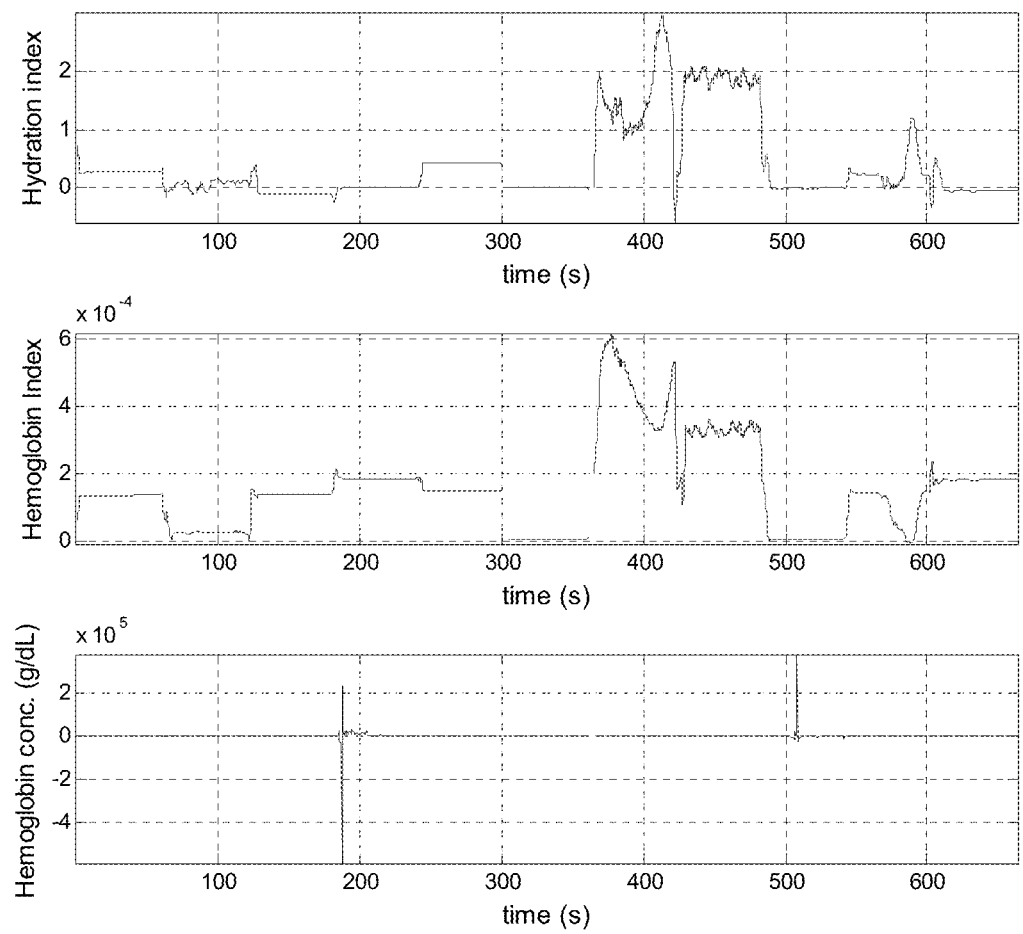
FIG. 8D is a graph displaying hydration indices (top), hemoglobin indices (middle), and hemoglobin concentration indices (bottom) derived from optical data detected during the second trial from the tissues of the user and the non-tissue materials.

FIG. 8D is a graph displaying hydration indices (top), hemoglobin indices (middle), and hemoglobin concentration indices (bottom) derived from optical data detected during the second trial from the tissues of the user and the non-tissue materials.

Figure 8E:
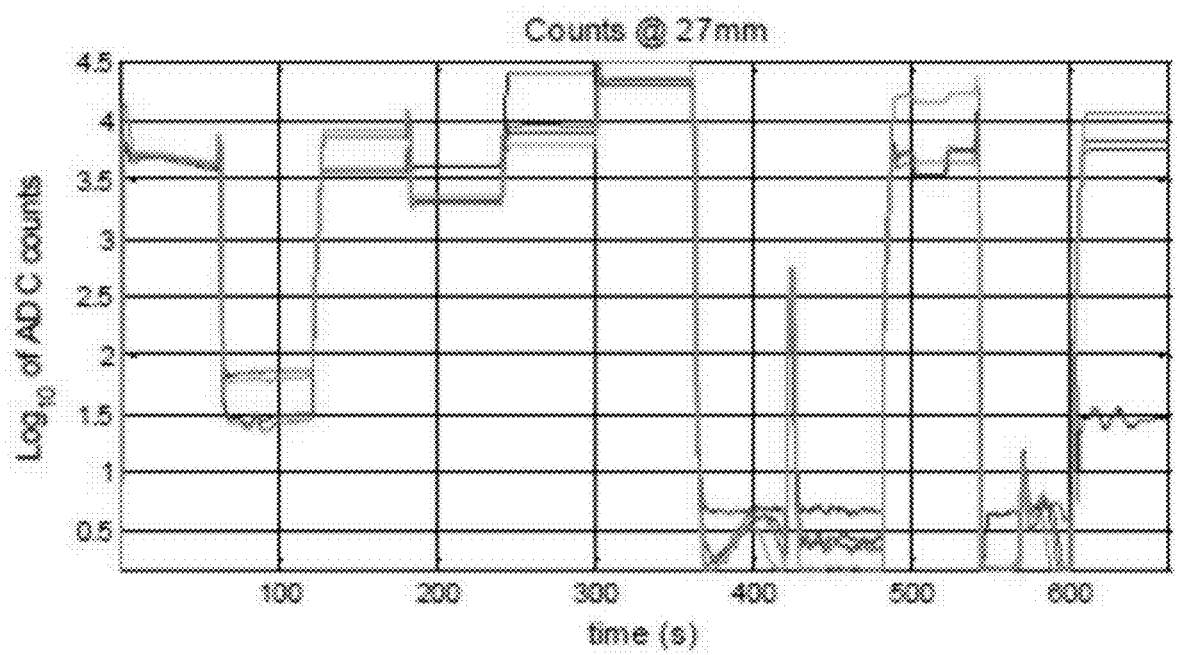
FIG. 8E is a graph displaying the common logarithm of the ADC counts corresponding to optical data detected from the tissues of the user and the non-tissue materials of the first trial at a 27 mm LED to photodiode separation distance.

FIG. 8E is a graph displaying the common logarithm of the ADC counts corresponding to optical data ($D_{ijm}$) detected from the tissues of the user and the non-tissue materials of the first trial wherein the optical emitter and optical photodetector are separated by a distance of twenty-seven mm.

Figure 9A:
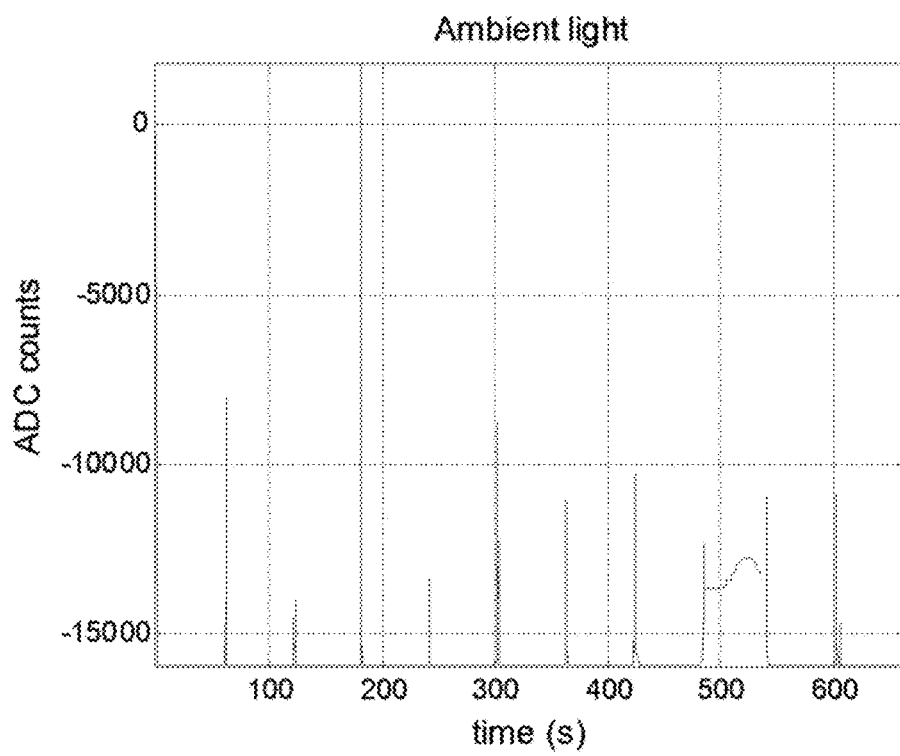
FIG. 9A is a graph displaying raw ADC ambient light counts corresponding to optical data detected, during a third trial, from tissues of a user and non-tissue materials.

FIG. 9A is a graph displaying raw ADC ambient light counts corresponding to optical data detected, during the third trial, from tissues of a user and non-tissue materials wherein the optical emitter and optical photodetector are separated by a distance of fifteen millimeters (mm). Signal spikes correspond with the movement of the device 200 from one tissue to another, one tissue to a non-tissue material, or from one non-tissue material to another. The first signal spike corresponds to the movement of the device 200 from the left calf of a user to the right calf of the user, the second spike corresponds to the movement of the device 200 from the right calf of the user to the right forearm of the user, the third spike corresponds to the movement of the device 200 from the right forearm of the user to the palm of the right hand of the user, the fourth spike corresponds to the movement of the device 200 from the palm of the right hand of the user to a white laminate tabletop, the fifth spike corresponds to the movement of the device 200 from the white laminate tabletop to an interior of a backpack, the sixth spike corresponds to the movement of the device 200 from the interior of the backpack to a an interior of a canvas bag, the seventh spike corresponds to the movement of the device 200 from the interior of the canvas bag to a rubber shoe sole, the eighth spike corresponds to the movement of the device 200 from the rubber shoe sole to a transparent bottle filled water, the ninth spike corresponds to the movement of the device 200 from the transparent bottle filled water to a foam headphone, and the tenth spike corresponds to the movement of the device 200 from the foam headphone to a wrapper of a food bar.

Figure 9B:
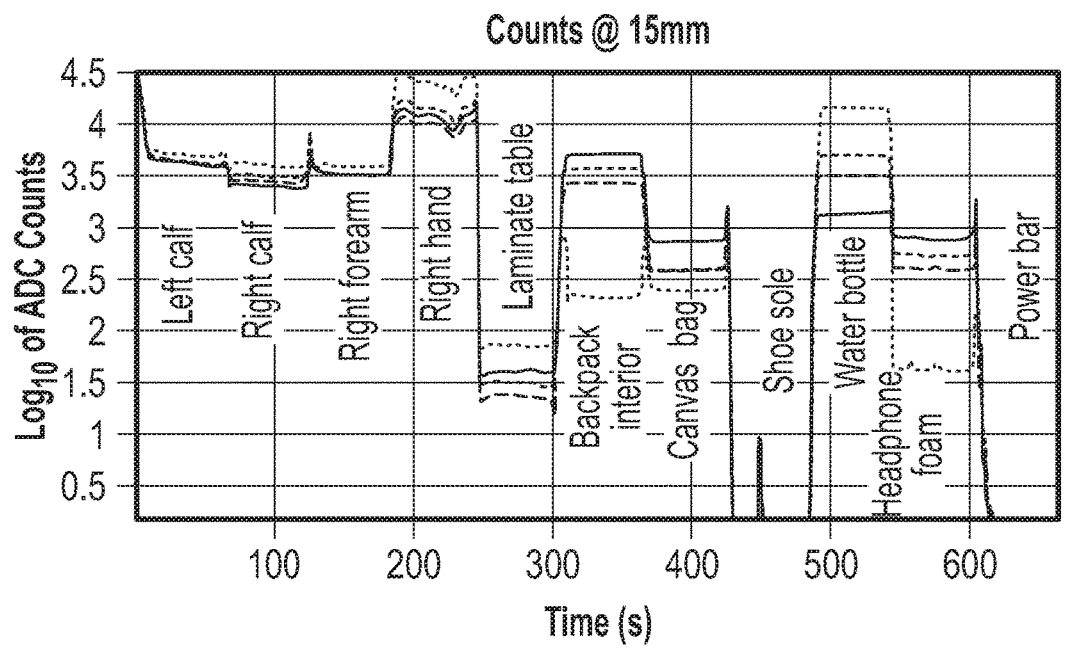
FIG. 9B is a graph displaying the common logarithm of the optical data ($D_{ijm}$) at a 15 mm LED to photodiode separation distance.

FIG. 9B is a graph displaying the common logarithm of the optical data ($D_{ijm}$). As with previous data, signal spikes correspond with the movement of the device 200 from one tissue to another, one tissue to a non-tissue material, or from one non-tissue material to another. From the obtained optical data, $\mu_a$ and $P_k(t)$ of each tissue and non-tissue material were calculated and HbF and HbConc were determined.

Figure 9C:
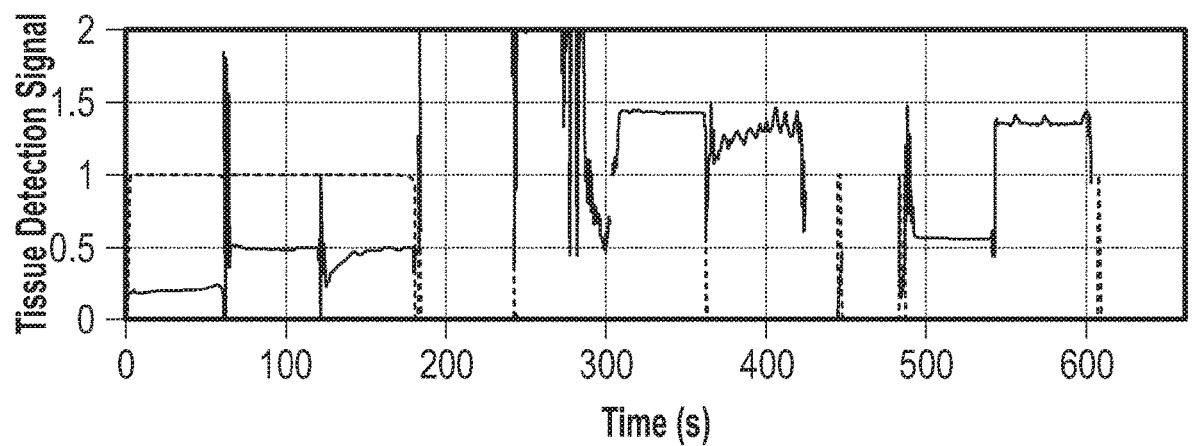
FIG. 9C is a graph displaying tissue detection signals derived from optical data detected during the third trial from the tissues of the user and the non-tissue materials.

FIG. 9C is a graph displaying tissue detection signals derived from optical data detected during the third trial from the tissues of the user and the non-tissue materials. As with previous data, signal spikes correspond with the movement of the device 200 from one tissue to another, one tissue to a non-tissue material, or from one non-tissue material to another.

Figure 9D:
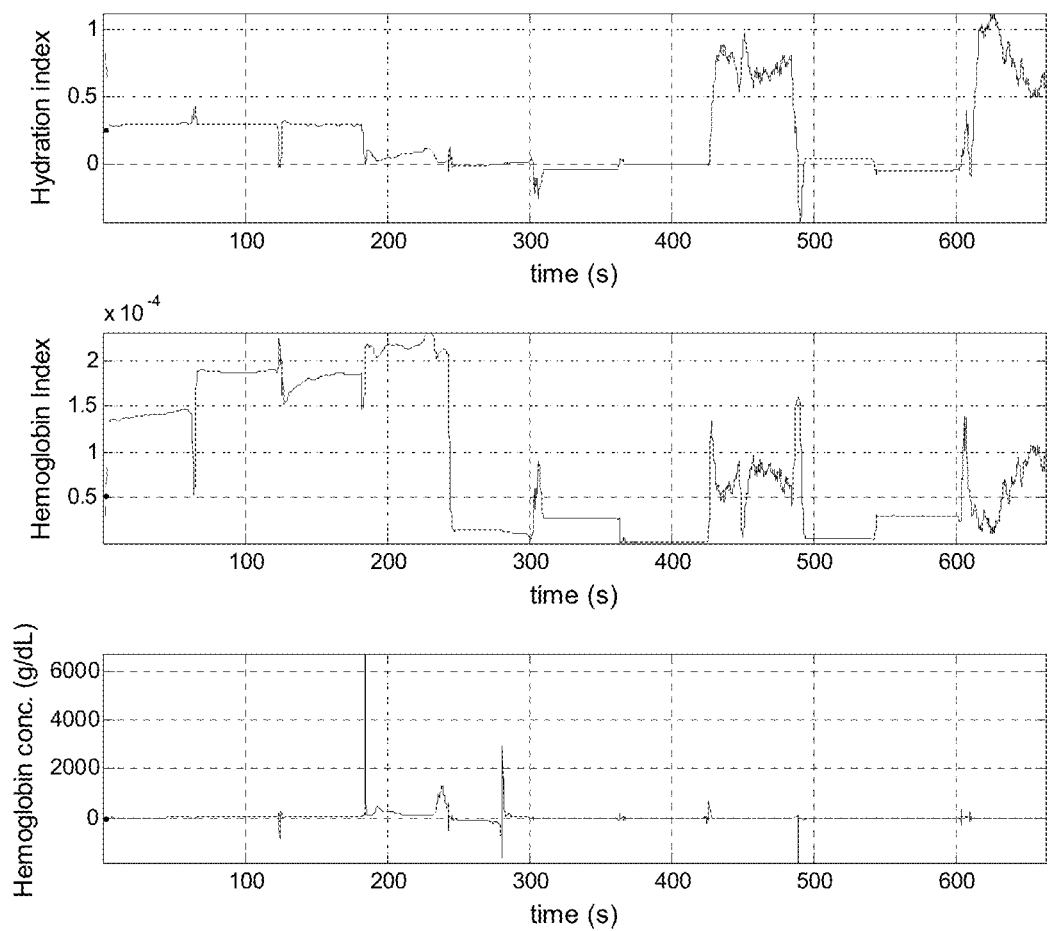
FIG. 9D is a graph displaying hydration indices (top), hemoglobin indices (middle), and hemoglobin concentration indices (bottom) derived from optical data detected during the third trial from the tissues of the user and the non-tissue materials.

FIG. 9D is a graph displaying hydration indices (top), hemoglobin indices (middle), and hemoglobin concentration indices (bottom) derived from optical data detected during the third trial from the tissues of the user and the non-tissue materials.

Figure 9E:
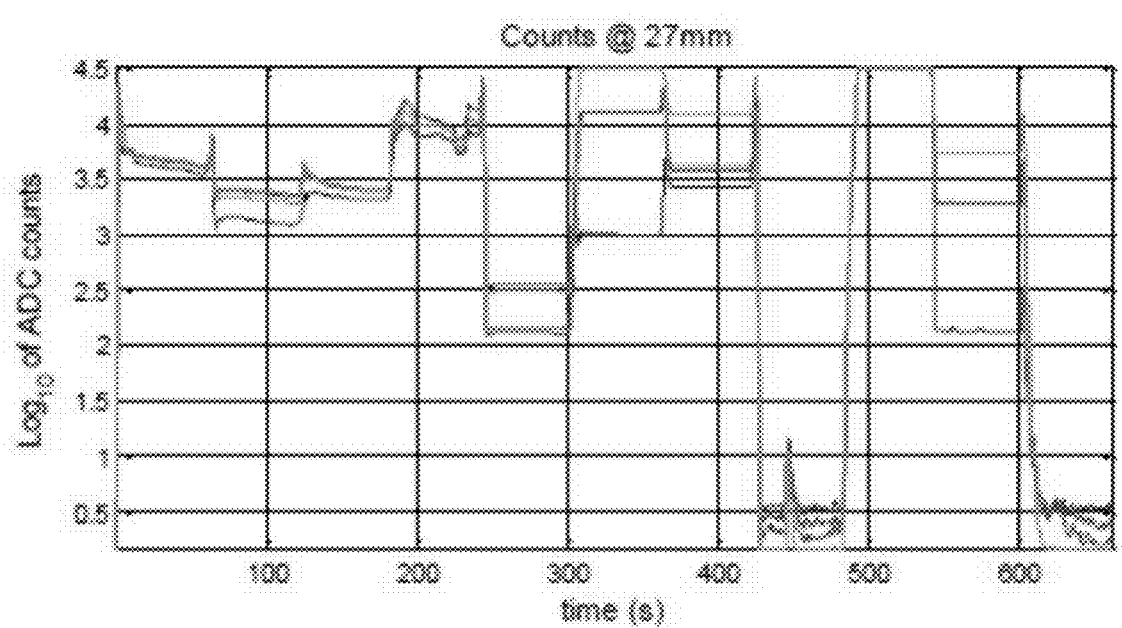
FIG. 9E is a graph displaying the common logarithm of the ADC counts corresponding to optical data detected from the tissues of the user and the non-tissue materials of the third trial at a 27 mm LED to photodiode separation distance.

FIG. 9E is a graph displaying the common logarithm of the ADC counts corresponding to optical data detected from the tissues of the user and the non-tissue materials of the third trial wherein the optical emitter and optical photodetector are separated by a distance of twenty-seven mm. As with the previous data, signal spikes correspond with the movement of the device 200 from one tissue to another, one tissue to a non-tissue material, or from one non-tissue material to another.

Figure 10A:
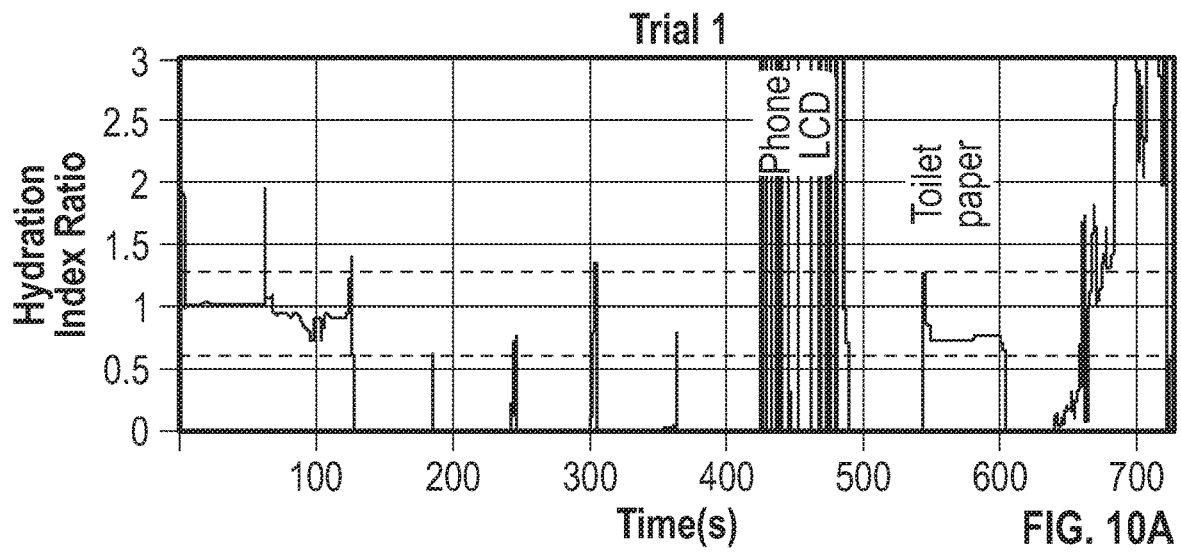
FIGS. 10A-I are graphs displaying the combined hydration index ratios (FIGS. 10A-C), hemoglobin index ratios (Hb fraction ratio, FIGS. 10D-F), and hemoglobin concentration index ratios (Hb conc. Ratio, FIGS. 10G-I) of the tissue and non-tissue materials from the first, second, and third.
Figure 10B:
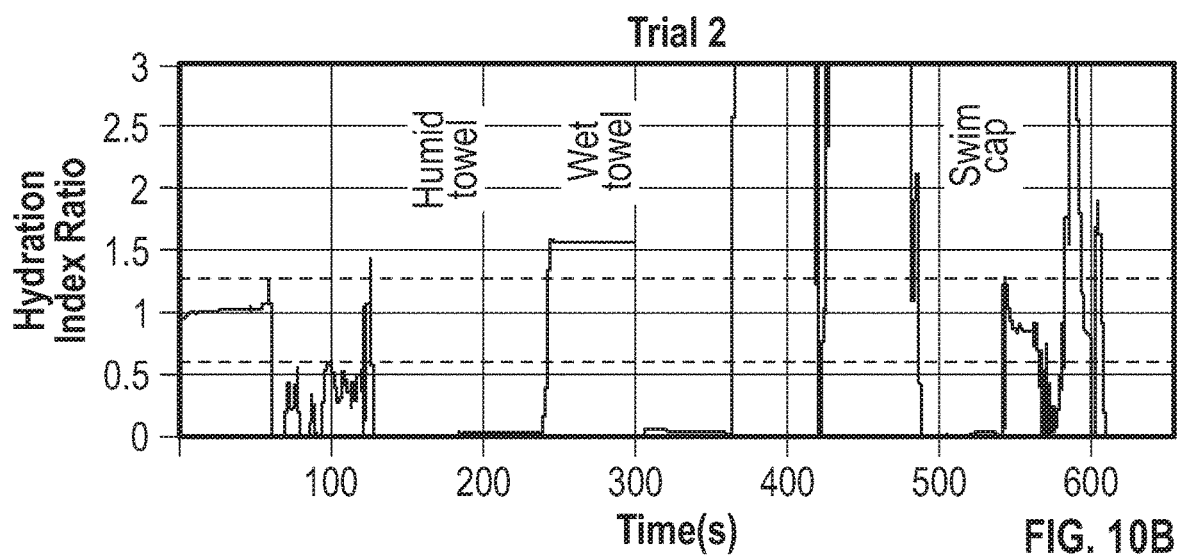
Figure 10C:
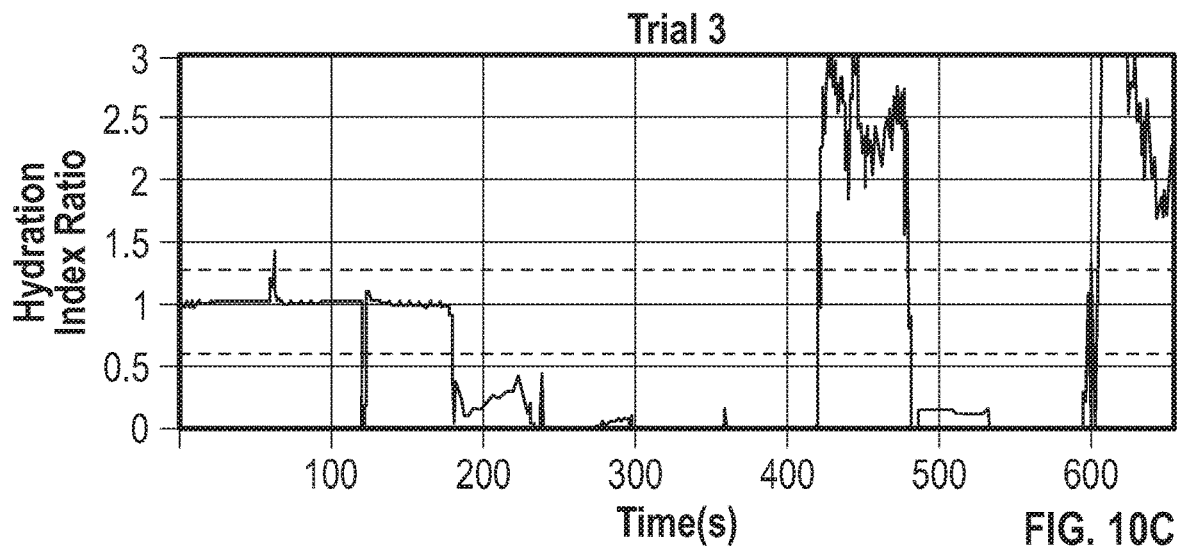
Figure 10D:
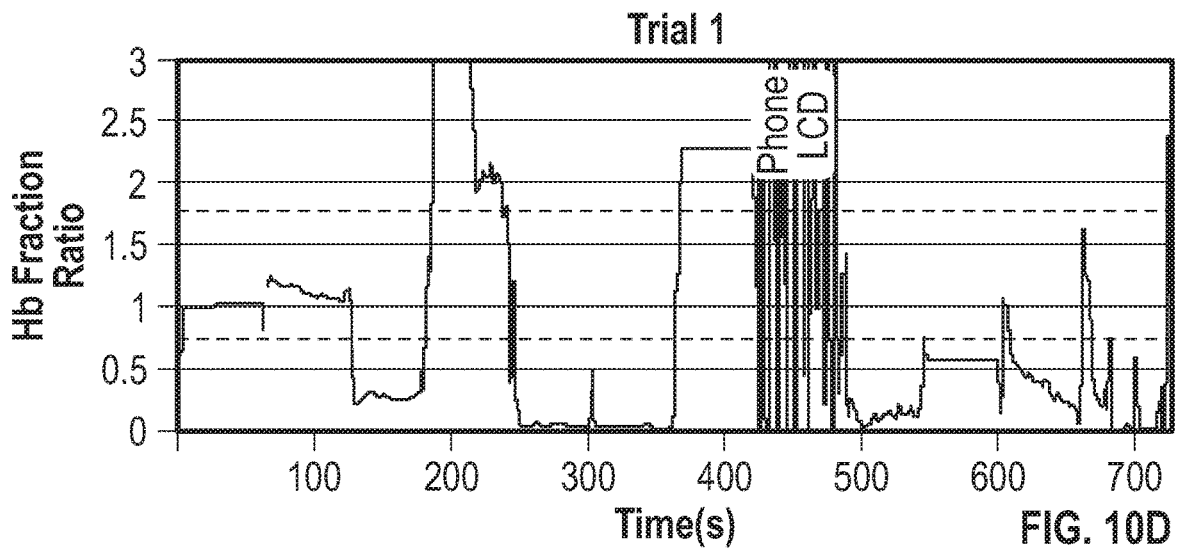
Figure 10E:
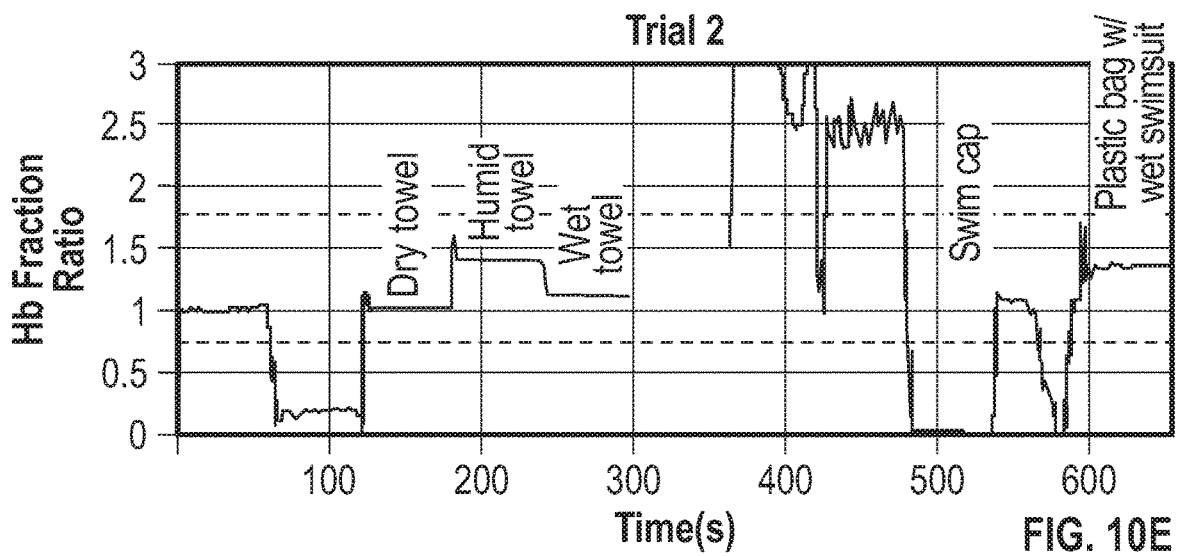
Figure 10F:
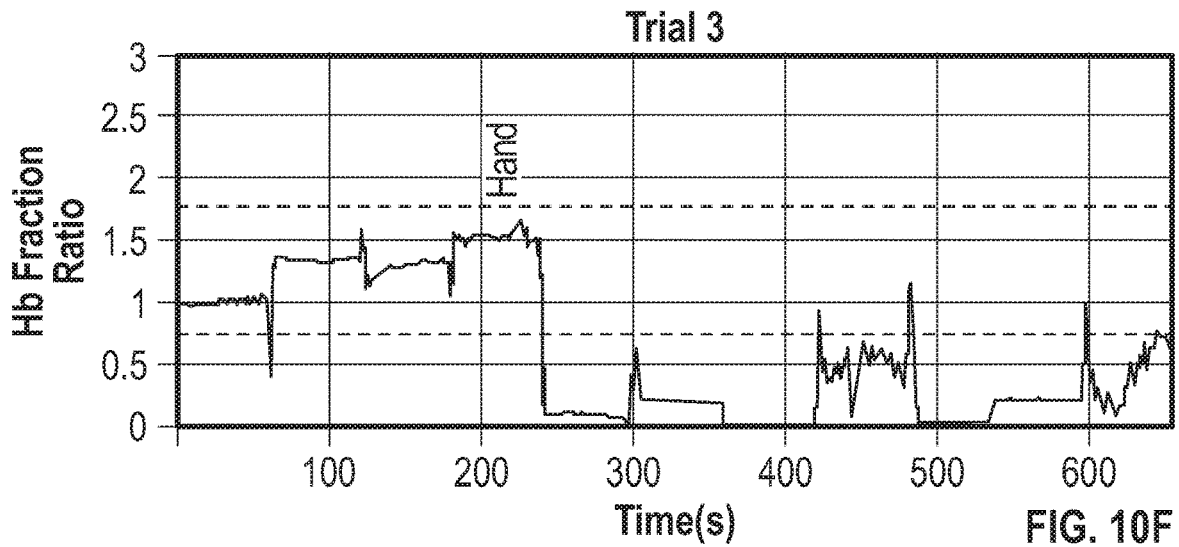
Figure 10G:
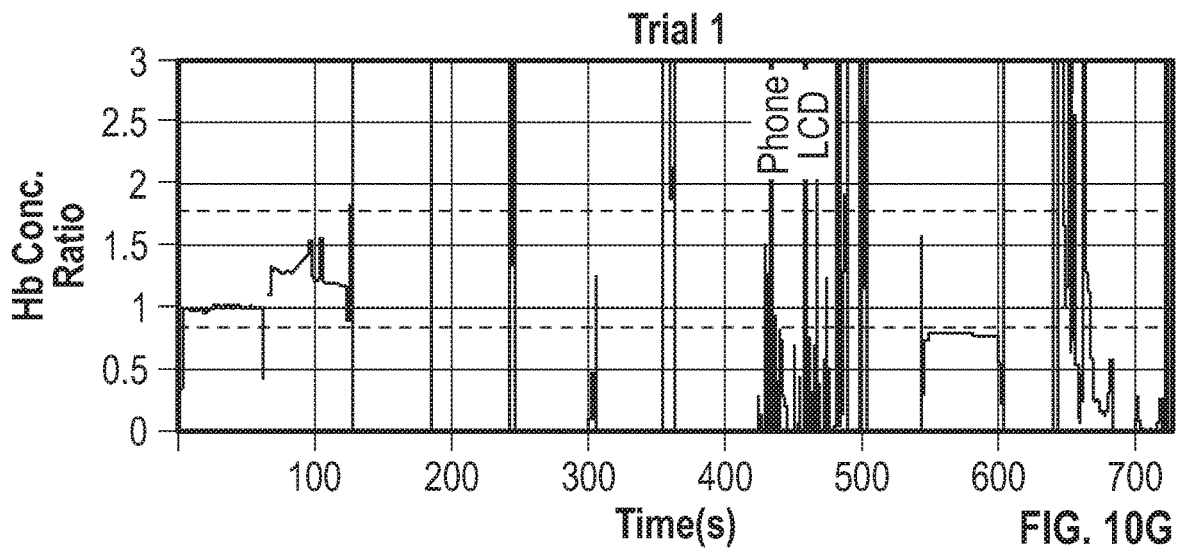
Figure 10H:
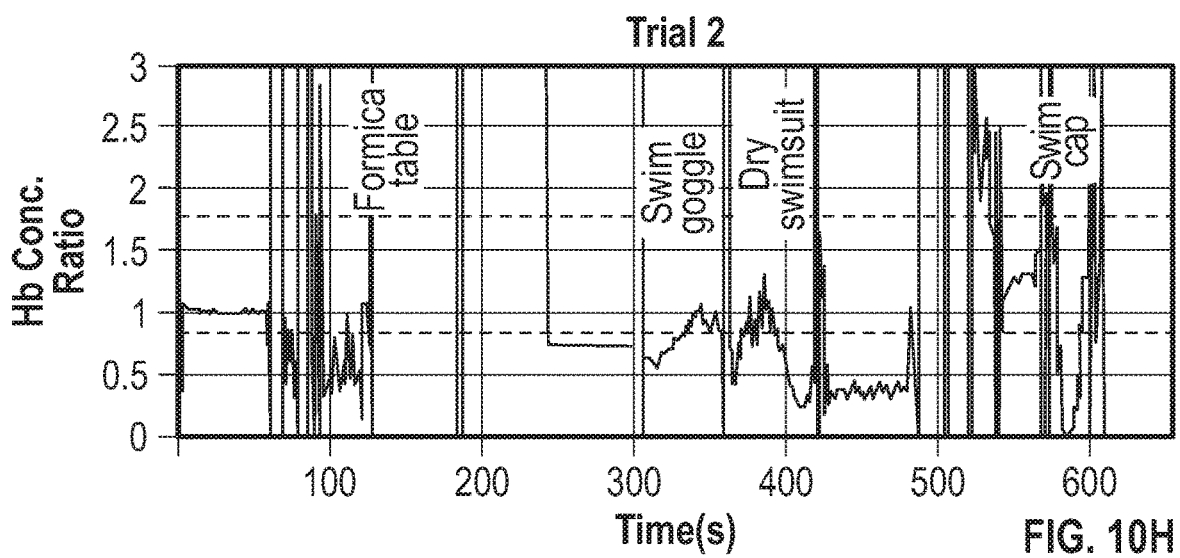
Figure 10I:
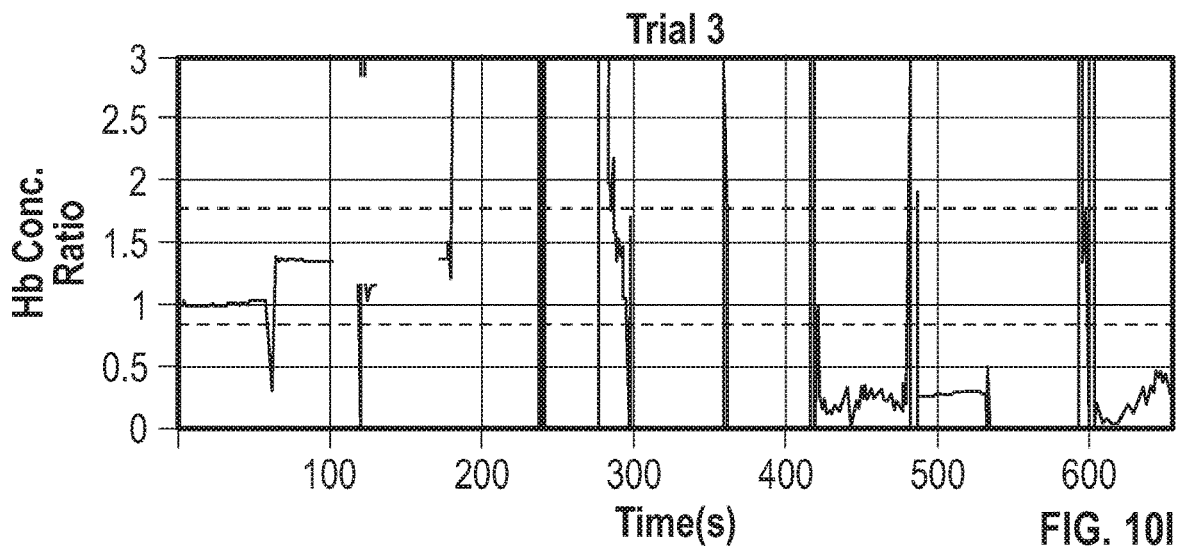

FIGS. 10A-I are graphs displaying the combined hydration index ratios (FIGS. 10A-C), hemoglobin index ratios (HbF ratio, FIGS. 10D-F), and hemoglobin concentration index ratios (HbConc Ratio, FIGS. 10G-I) of the tissue and non-tissue materials from the first trial (FIGS. 10A, 10D, 10G), second trial (FIGS. 10B, 10E, 10H), and third trial (FIGS. 10C, 10F, 10I). Optical tissue detection thresholds are shown as in each graph as dashed purple lines. Non-tissue materials that were misidentified as tissue using the individual threshold values are labeled in red. As can be seen, non-tissue materials that generate a large amount of light, such as a phone LCD screen, or contain moisture, such as a damp or wet towel, are potential sources of false positives during optical tissue detection using device 200. As with previous data, signal spikes correspond with the movement of the device 200 from one tissue to another, one tissue to a non-tissue material, or from one non-tissue material to another. The graphs in FIGS. 10A-I allow for determination that HbConc and HbF parameters are sufficient to classify materials as tissue or non-tissue, since their combination resulted in the lowest false-positive rate (only the swim cap was incorrectly identified as tissue when HbConc and HbF signals are taken into account), and also to conclude that including the hydration index data would not further improve the classification task.

In at least one example, the devices 100, 200, 300 can generate and collect optical tissue data for more than one user. When the devices 100, 200, 300 can generate and collect optical tissue data for more than one user, the devices 100, 200, 300 can further use the optical tissue data of each user to generate a corresponding profile for each user. To generate a profile of each user of the device 100, 200, 300 the following method can be implemented.

First each user of the device 100, 200, 300 can create a user account in a non-transitory computer-readable storage medium located in the electronic device and in a non-transitory computer-readable storage medium located in the device 100, 200, 300. The user account can contain information such as, for example, the name of the user, the age, height and weight of the user, the home and billing address of the user, the e-mail address of the user, the phone number of the user, and other similar user account information. The non-transitory computer-readable storage mediums store information regarding user and optical tissue data of the user generated and collected during exercise routines and can communicate the information from the device 100, 200, 300 to the electronic device as described above. Second, each user can perform N routines, where N is a number of times a routine is performed by the user. The routines can be exercise routines. The exercise routines can be, for example, one of running, cycling, swimming, strength training, hiking, or any other suitable exercise routine. Further, the exercise routines can be specific training routines. The specific training routines can be, for example, cardiovascular training routines, endurance training routines, zone training, or any other suitable training routine. In each of N exercise and/or training routines, optical tissue data corresponding to any one or more of oxygenated hemoglobin concentration, deoxygenated hemoglobin concentration, total hemoglobin concentration, hemoglobin index, hemoglobin concentration index, hydration index, lactate threshold, and ventilatory threshold is generated and collected and communicated between the device 100, 200, 300 and electronic device as described above. Upon reaching N routines, the optical tissue data can be analyzed and used by a processor, under instruction of the non-transitory computer-readable storage medium located in the electronic device, to generate a user profile. The user profile is associated with the user account and the tissue data can be further associated with user characteristics (age, gender, height, weight, etc). In at least one example, N is greater than 1. Alternatively, N is greater than 5, alternatively, greater than 10, alternatively greater than 20. Alternatively, the user profile can be generated after every routine is performed and corresponding data generated, collected, and analyzed.

The device 100, 200, 300 and electronic device can further assign generated, collected and analyzed optical tissue from a routine to a specific user profile without prior input identifying the user as the source of the optical tissue data. Here, the electronic device can compare the optical tissue data generated, collected and analyzed from a routine and compare it to each user profile. Upon comparison of the routine data to each user profile by the either or both of the non-transitory computer-readable storage medium located in the electronic device and in the non-transitory computer-readable storage medium located in the device 100, 200, 300, the data associated with that routine can be assigned to the user based on the similarity between the routine data and the user profile. Such correlation of data from a single routine data and the stored user profiles can thereby create a biometric recognition process because each user can have a distinct user profile can on the user's individual optical tissue data generated, collected, and analyzed over N routines.

Figure 12:
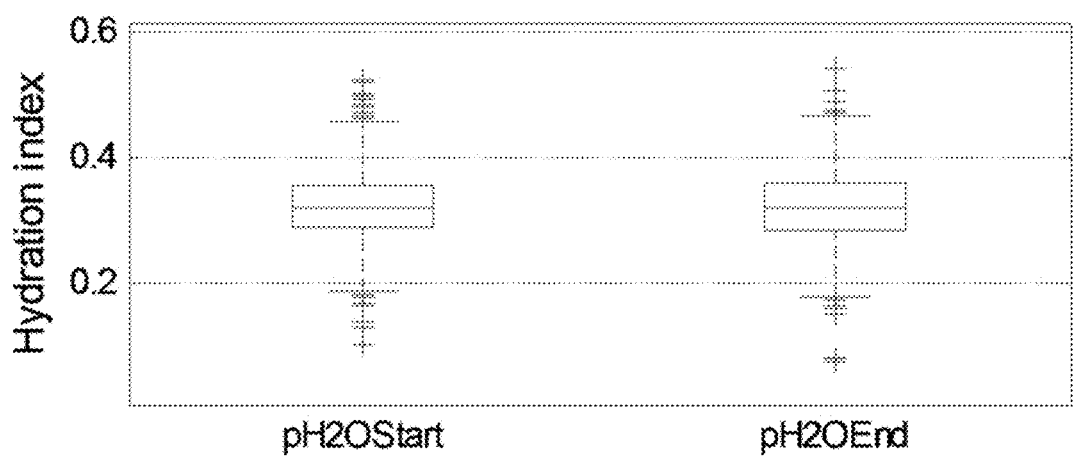
FIG. 12 is a graph displaying two ranges of the hydration index (y-axis) compiled from optical data of the user profiles using an exemplary non-invasive optical tissue detection device according to the disclosure herein.

An example of a user profile assessment of six hundred ten (610) user profiles is described below with respect to FIGS. 11-13. The data used to generate FIGS. 11-13 was obtained using the following procedure with device 200. As stated above, the data illustrated in FIGS. 13-15 was generated from data corresponding to the 610 individual user profiles, each user profile constituting a data set. For each user profile data set, optical tissue data, as described above, was calculated during the first 35 seconds ("Start") of a routine and at the 3.6 minute mark ("End") of a user routine. The whiskers of the plotted boxplots shown in FIGS. 11-13 are then used to determine the HbConc and HbF threshold values. These correspond to the fences of the aggregate data set, resulting in a 99.3% sensitivity to optical tissue and a false positive rate of 7.4%. That is, the device 200 is shown to have a 99.3% sensitivity to tissue detection and only 7.4% of the data can be attributed to non-tissue materials. As known to those skilled in the art, the upper fence of a data set is given by the third quartile of the data set plus 1.5 times the interquartile range, while the lower fence is given by the first quartile minus 1.5 times the interquartile range.

The threshold values are determined as follows: HbFMIN is given by the lower fence (whisker) of HbFStart shown in FIG. 11 and HbFMAX is given by the higher fence (whisker) of HbFStart. HbConcMIN is given by the lower fence (whisker) of HbConcStart shown in FIG. 13 and HbConcMAX is given by the higher fence (whisker) of HbConcStart. The End values (HbFEnd and HbConcEnd) are shown for comparison, allowing one to confirm that the parameter fence values do not vary greatly from the start to the end of activities. Nevertheless, the start values were preferred given that tissue detection is expected to be most useful in the beginning of an activity, as a method to determine that the device is attached to tissue and, thus, ready to start data collection.

In FIG. 11, a graph displaying two ranges of hemoglobin index (y-axis) compiled from optical data of the 610 user profiles at Start and at End is shown. As can be seen, the Start and End range data do not appreciably change, but does slightly increase from Start to End. As can be seen the 610 user profiles generated hemoglobin index range have a lower "whisker" of 2.30e-5 and an upper whisker of 2.54e-4. Numeric analysis of the data further reveal that the hemoglobin index has a value of 1.86e-4 in the top 1-percentile and 2.32e-4 in the top 99-percentile at Start.

For a whisker of length w. The default is a w of 1.5. Points are drawn as outliers if they are larger than q3+w(q3−q1), wherein q3 corresponds to the third quartile and q1 corresponds to the first quartile, or smaller than q1−w(q3−q1), where q1 and q3 are the 25th and 75th percentiles, respectively. The default of 1.5 corresponds to approximately +/−2.7σ and 99.3% coverage assuming a normal data distribution. The plotted whisker extends to the adjacent value, which is considered to be the most extreme data value that is would be indicative of a tissue of a user. Using the upper and lower whiskers as the threshold corresponding to accepting approximately 99.3% of user data as tissue, and those outside the whisker range are considered to be non-tissue material(s). In the case of individual users, tissue data can be used from that user alone. Using tissue data from a single user may result in a tighter range between top and bottom whiskers for both parameters for the individual user. In one example for one user, the tighter ranges were 9.0e-5<HbF<2.1E-4, and 18.4<HbConc<37.8. Whisker ranges can also be used for biometric recognition or identification of user data.

In FIG. 12, a graph displaying two ranges of hydration index (y-axis) compiled from optical data of the 610 user profiles at Start and at End is shown. As can be seen, the Start and End range data do not appreciably change, but does slightly increase from Start to End. As can be seen, the 610 user profiles generated hydration index range having a lower "whisker" of $1.85 \times 10^{-1}$ and an upper whisker of $4.59 \times 10^{-1}$. Numeric analysis of the data further reveals that the hydration index has a value of $2.19 \times 10^{-1}$ in the top 1-percentile and $3.32 \times 10^{-1}$ in the top 99-percentile at Start.

In FIG. 13, a graph displaying two ranges of hemoglobin concentration (y-axis) compiled from optical data of the 610 user profiles at Start and at End is shown. As can be seen, the Start and End range data do not appreciably change, but does slightly increase from Start to End. As can be seen the 610 user profiles generated hemoglobin concentration index range having a lower "whisker" of 4.47 and an upper whisker of 40.16 Numeric analysis of the data further reveals that the hemoglobin concentration index has a value of 28.39 in the top 1-percentile and 49.57 in the top 99-percentile at START.

In each of FIGS. 11-13, compilation of the optical data of the 610 user profiles generated a broad data value distribution. It should be noted, however, that each individual user profile would have corresponding data that is distinct within the ranges outlined above. Because each user profile will have a distinct data range corresponding to optical tissue data from a corresponding set of N routines, each user can be compared to the range of other users and can be discriminated from other users. Such discrimination between users can allow for determination of which user generated to the optical tissue data and thus allow for biometric recognition of each individual user. Such discrimination can also result in an improved ability to distinguish a given user from non-tissue material, reducing the false-positive rate and, thus, improve the specificity of the device.

Figure 14:
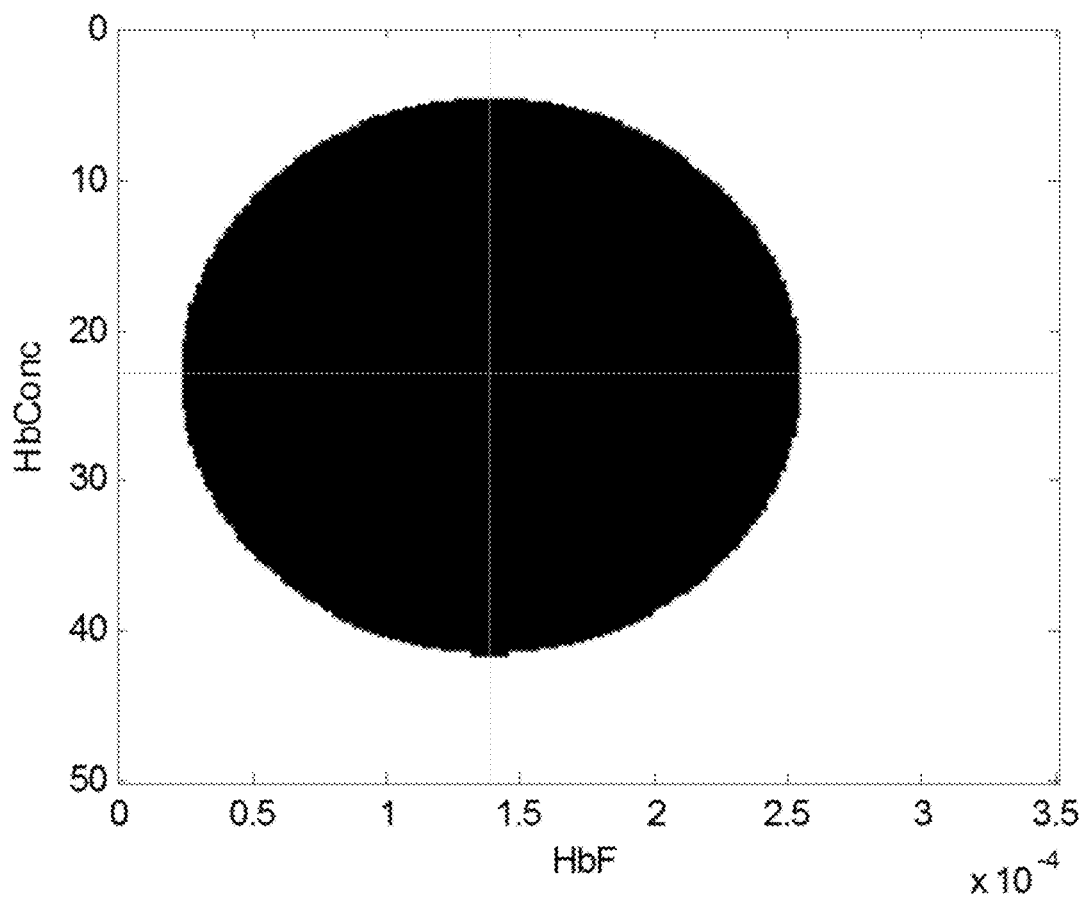
FIG. 14 is a plot showing relative values of total hemoglobin (HbF, x-axis) and hemoglobin concentration index (HbConc, y-axis) with the dark circular region indicating the range of HbConc and HbF values corresponding to positive tissue detection.
Figure 15:
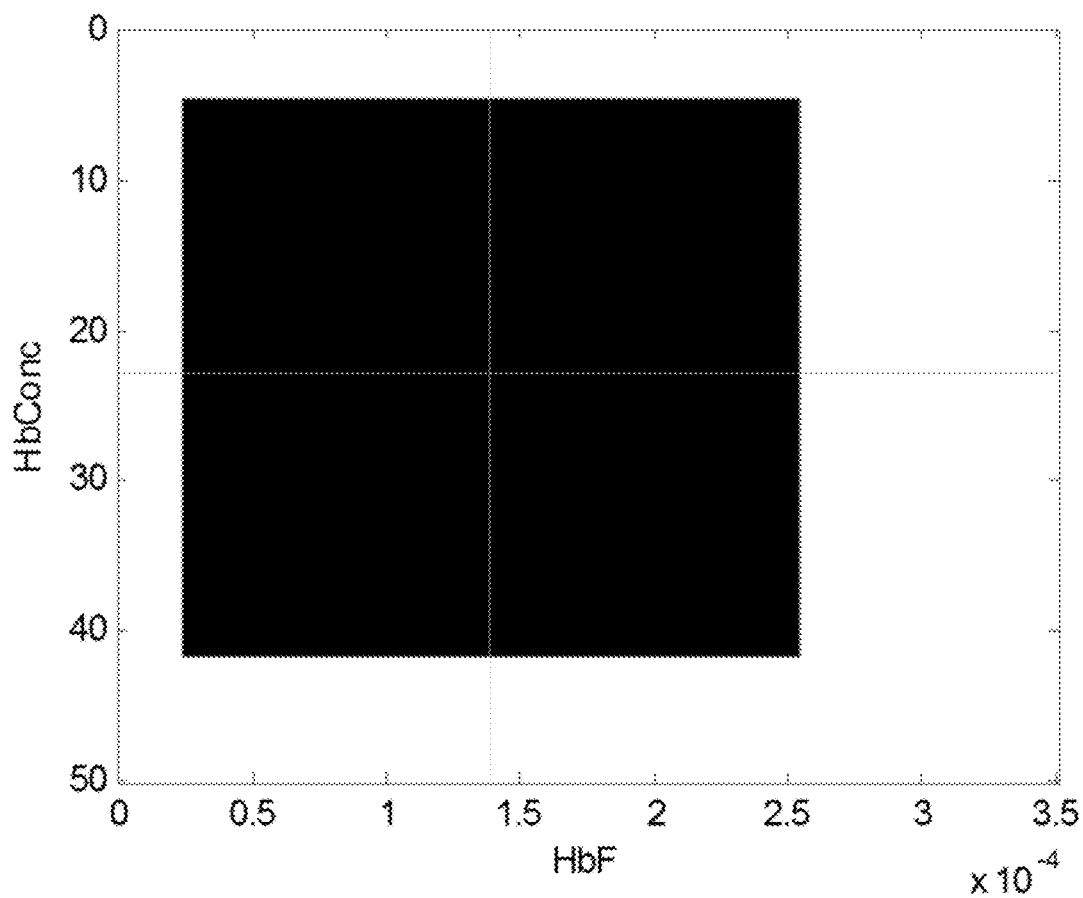
FIG. 15 is another plot showing relative values of total hemoglobin (HbF, x-axis) and hemoglobin concentration index (HbConc, y-axis) with the dark rectangular region indicating the range of HbConc and HbF values corresponding to positive tissue detection.

FIGS. 14 and 15 are plots showing relative values of total hemoglobin concentration (HbF, x-axis) and hemoglobin concentration index (HbConc, y-axis) indicative of optical data obtained from a tissue of a user. In FIG. 16, the dark ellipsis comprises a range of total hemoglobin concentration and hemoglobin concentration index values indicative of a tissue using the rule by which tissue is detected when the Error value, given by sqrt(HbFError^2+HbConcError^2), is larger than 0.5. The point at which the horizontal and vertical line passing through the dark ellipsis meet denotes the center (or target) of tissue detection bands (HbF=HbFTarget and HbConc=HbConcTarget) as previously described.

In FIG. 15, the dark rectangle comprises a range of total hemoglobin concentration and hemoglobin concentration index values indicative of a tissue using the rule by which tissue is detected when HbConcMIN<HbConc<HbConcMAX and HbFMIN<HbF<HbFMAX. The point at which the horizontal and vertical line passing through the dark rectangle meet denotes the center (or target) of tissue detection bands (HbF=HbFTarget and HbConc=HbConcTarget) as previously described.

In another example the error values HbConcError and HbFError are translated by the estimated mean values of HbConc and HbF, respectively, and linearly-transformed by matrix multiplication with $A^{-1/2}U^T$, the eigenvalue and eigenvector matrices of the covariance matrix of X. These linear operations corresponds to transforming the ellipsis of FIG. 14 into a circle centered at the origin of the coordinate system, with the benefit of allowing us to set an error function (and boundary conditions) better capable to distinguishing between tissue and non-tissue materials, further improving the specificity and sensitivity of the device 100, 200 and 300.

What is claimed is:

1. An apparatus operable to optically detect tissue, the apparatus comprising:
    at least one light source operable to emit light of at least three wavelengths into a material, at least one of the at least three wavelengths being about 980 nanometers;
    at least one photodetector operable to detect at least a portion of the light reflected from the material;
    a non-transitory medium coupled with a processor and storing instructions for determining whether the material is a biological tissue of a subject or a non-tissue material and for launching an activity when the material is the biological tissue; and
    the processor coupled with the at least one light source and the at least one photodetector, the processor operable to execute the instructions, stored in the non-transitory medium, for:
        determining whether the material is the biological tissue or the non-tissue material based on the light detected by the at least one photodetector,
        when the material is the biological tissue, launching the activity, wherein the activity includes the at least one photodetector recording measurements, and the non-transitory medium is operable to store the recorded measurements, and
        when the material is the non-tissue material, not launching the activity, and initiating an alert by an output device to check placement of the apparatus,
    wherein the at least one light source emits light at predetermined intervals to determine if the at least one photodetector is proximate to the tissue, and
    wherein the at least one light source and the at least one photodetector are operable to be enabled by further activation, wherein the further activation includes the processor detecting a movement.

2. The apparatus of claim 1, wherein the at least one light source emits light in at least three wavelengths between about 600 nanometers to about 1100 nanometers.

3. The apparatus of claim 1, wherein the at least one light source is coupled to an article of clothing that is operable to secure the at least one light source to a body part of the subject.

4. The apparatus of claim 1, further comprising a transmitter that is operable to transmit the stored measurements to an electronic device.

5. The apparatus of claim 1, wherein the processor is further operable to determine the subject from a plurality of previously identified subjects based on the detected light.

6. The apparatus of claim 1, wherein the processor is further operable to filter optical signals that do not correspond to detected light from the tissue of the subject.

7. The apparatus of claim 6, wherein the filtered optical signals correspond to light emitted from any one or more of plastics, polymeric materials, fabrics, textiles, non-tissue surfaces, or cellulosic materials.

8. The apparatus of claim 1, wherein the at least one light source, the at least one photodetector and the processor are coupled to an article of clothing that comprises one of a strap, sleeve, jacket, wrist strap, glass, hat, cap, helmet or wrap configured for securement to a body part of the subject corresponding to the tissue of the subject.

9. The apparatus of claim 1, wherein the at least one light source is a light emitting diode (LED).

10. The apparatus of claim 1, wherein the at least one photodetector generates optical tissue data that comprises data which is used by one or both of the processor and a processor of an electronic device to calculate one or more of hydration index, oxygenated hemoglobin concentration, deoxygenated hemoglobin concentration, total hemoglobin concentration, hemoglobin index, hemoglobin concentration index, lactate threshold, and ventilatory threshold.

11. A biometric recognition device, comprising the apparatus of claim 1, wherein the biometric recognition device is configured for detection and identification of different subjects.

12. A system operable to optically detect tissue, the system comprising:
    a tissue detection device comprising:
        at least one light source operable to emit light of at least three wavelengths into a material, at least one of the at least three wavelengths being about 980 nanometers; and
        at least one photodetector operable to detect at least a portion of the light reflected from the material; and
    an electronic device coupled to the tissue detection device and operable to transmit signals to activate the at least one light source and receive data from the at least one photodetector, the electronic device comprising:
        a non-transitory medium coupled with a processor and storing instructions for determining whether the material is a biological tissue of a subject or a non-tissue material and for launching an activity when the material is the biological tissue; and
        the processor coupled with the at least one light source and the at least one photodetector, the processor operable to execute the instructions, stored in the non-transitory medium, for:
            determining whether the material is the biological tissue or the non-tissue material based on the light detected by the at least one photodetector,
            when the material is the biological tissue, launching the activity, wherein the activity includes the at least one photodetector recording measurements, and the non-transitory medium is operable to store the recorded measurements, and
            when the material is the non-tissue material, not launching the activity, and initiating an alert by an output device to check placement of the apparatus,
    wherein the at least one light source emits light at predetermined intervals to determine if the at least one photodetector is proximate to the tissue, and wherein the at least one light source and the at least one photodetector are operable to be enabled by further activation, wherein the further activation includes the processor detecting a movement.

* * * * *